US012582342B2

(12) United States Patent
Grouchy et al.

(10) Patent No.: US 12,582,342 B2
(45) Date of Patent: Mar. 24, 2026

(54) METHOD AND SYSTEM TO ASSESS PULMONARY HYPERTENSION USING PHASE SPACE TOMOGRAPHY AND MACHINE LEARNING

(71) Applicant: Analytics for Life Inc., Toronto (CA)

(72) Inventors: Paul Grouchy, Toronto (CA); Meng Lei, North York (CA); Ian Shadforth, Morrisville, NC (US); Sunny Gupta, East York (CA); Timothy Burton, Toronto (CA); Shyamlal Ramchandani, Kingston (CA)

(73) Assignee: Analytics for Life Inc., Toronto (CA)

( * ) Notice: Subject to any disclaimer, the term of this patent is extended or adjusted under 35 U.S.C. 154(b) by 174 days.

(21) Appl. No.: 17/936,496

(22) Filed: Sep. 29, 2022

(65) Prior Publication Data

US 2023/0157618 A1 May 25, 2023

Related U.S. Application Data

(63) Continuation of application No. 16/429,593, filed on Jun. 3, 2019, now Pat. No. 11,471,090.

(Continued)

(51) Int. Cl.
*A61B 5/361* (2021.01)
*A61B 5/00* (2006.01)
(Continued)

(52) U.S. Cl.
CPC .............. *A61B 5/361* (2021.01); *A61B 5/316* (2021.01); *A61B 5/339* (2021.01); *A61B 5/7267* (2013.01);
(Continued)

(58) Field of Classification Search
CPC ......... A61B 5/361; A61B 5/316; A61B 5/339; A61B 5/7267; A61B 5/0536;
(Continued)

(56) References Cited

U.S. PATENT DOCUMENTS 6,135,966 A 10/2000 Ko
6,310,968 B1 10/2001 Hawkins et al.
(Continued)

FOREIGN PATENT DOCUMENTS

WO 2017/221221 12/2017

OTHER PUBLICATIONS

Cutri [The cardiac torsion as a sensitive index of heart pathology: A model study, Journal of the mechanical behavior of biomedical materials 55 (2016)] (Year: 2016).*

(Continued)

*Primary Examiner* — Oommen Jacob
(74) *Attorney, Agent, or Firm* — Meunier Carlin & Curfman LLC

(57) ABSTRACT

Phase space tomography methods and systems to facilitate the analysis and evaluation of complex, quasi-periodic system by generating computed phase-space tomographic images and mathematical features as a representation of the dynamics of the quasi-periodic cardiac systems. The computed phase-space tomographic images can be presented to a physician to assist in the assessment of presence or non-presence of disease. In some implementations, the phase space tomographic images are used as input to a trained neural network classifier configured to assess for presence or non-presence of pulmonary hypertension, including pulmonary arterial hypertension.

20 Claims, 11 Drawing Sheets

Related U.S. Application Data

(60) Provisional application No. 62/680,275, filed on Jun. 4, 2018.

(51) Int. Cl.

| | |
|---|---|
| *A61B 5/0536* | (2021.01) |
| *A61B 5/1455* | (2006.01) |
| *A61B 5/316* | (2021.01) |
| *A61B 5/339* | (2021.01) |
| *G06N 3/08* | (2023.01) |
| *G06T 3/4007* | (2024.01) |
| *G06T 11/00* | (2006.01) |

(52) U.S. Cl.
CPC .............. *G06N 3/08* (2013.01); *A61B 5/0536* (2013.01); *A61B 5/1455* (2013.01); *G06T 3/4007* (2013.01); *G06T 11/006* (2013.01); *G06T 2200/08* (2013.01); *G06T 2210/41* (2013.01)

(58) Field of Classification Search
CPC ...... A61B 5/1455; G06N 3/08; G06T 3/4007; G06T 11/006; G06T 2200/08; G06T 2210/41
See application file for complete search history.

(56) References Cited

U.S. PATENT DOCUMENTS

| | | | |
|---|---|---|---|
| 6,522,712 B1 | 2/2003 | Yavuz et al. | |
| 8,157,742 B2 | 4/2012 | Taylor et al. | |
| 8,923,958 B2 | 12/2014 | Gupta et al. | |
| 9,289,150 B1 | 3/2016 | Gupta et al. | |
| 9,408,543 B1 | 8/2016 | Gupta et al. | |
| 9,597,021 B1 | 3/2017 | Gupta et al. | |
| 9,655,536 B2 | 5/2017 | Gupta et al. | |
| 9,737,229 B1 | 8/2017 | Gupta et al. | |
| 2003/0028119 A1* | 2/2003 | Xue ...................... | A61B 5/339 600/523 |
| 2004/0081270 A1 | 4/2004 | Heuscher | |
| 2007/0086563 A1 | 4/2007 | Bruder | |
| 2009/0242776 A1 | 10/2009 | Kobashi et al. | |
| 2009/0274375 A1 | 11/2009 | Kavanau et al. | |
| 2011/0245675 A1 | 10/2011 | Yoshida et al. | |
| 2013/0096394 A1* | 4/2013 | Gupta ................... | A61B 5/341 600/301 |
| 2014/0029829 A1 | 1/2014 | Jiang et al. | |
| 2014/0207005 A1* | 7/2014 | Bukkapatnam ...... | A61B 5/7235 600/509 |
| 2015/0133803 A1 | 5/2015 | Gupta et al. | |
| 2015/0216426 A1 | 8/2015 | Burton et al. | |
| 2015/0297161 A1 | 10/2015 | Grass et al. | |
| 2015/0359601 A1 | 12/2015 | Sauer et al. | |
| 2016/0364861 A1 | 12/2016 | Taylor et al. | |
| 2016/0378936 A1 | 12/2016 | Burton et al. | |
| 2017/0045600 A1 | 2/2017 | Hsiao et al. | |
| 2017/0119272 A1* | 5/2017 | Gupta ..................... | A61B 5/30 |
| 2018/0000371 A1 | 1/2018 | Gupta et al. | |
| 2018/0033991 A1 | 2/2018 | Yamashita | |
| 2018/0078146 A1 | 3/2018 | Shadforth et al. | |
| 2019/0026430 A1 | 1/2019 | Grouchy et al. | |
| 2019/0117164 A1 | 4/2019 | Gupta et al. | |
| 2019/0200893 A1 | 7/2019 | Grouchy et al. | |
| 2019/0365265 A1 | 12/2019 | Grouchy et al. | |
| 2023/0157618 A1* | 5/2023 | Grouchy .............. | G06T 11/008 600/425 |

OTHER PUBLICATIONS

Freund, Y., et al., "A decision-theoretic generalization of on-line learning and an application to boosting," Proceedings of the Second European Conference on Computational Learning Theory, 1995, 15 pages.

International Search Report and Written Opinion, dated Oct. 1, 2019, received in connection with International Patent Application No. PCT/IB2019/054581.

Lungu, Angela, et al. "Diagnosis of pulmonary hypertension from magnetic resonance imaging-based computational models and decision tree analysis." Pulmonary circulation 6.2 (2016): 181-190.

Sabouri, Sepideh, Hamid SadAbadi, and Nader Jafarnia Dabanloo. "Neural network classification of body surface potential contour map to detect myocardial infarction location." 2010 Computing in Cardiology. IEEE, 2010.

* cited by examiner

NORMAL HEART

PULMONARY ARTERIES
(TO LUNGS)

AORTA

PULMONARY VEINS
(FROM LUNGS)

RIGHT ATRIUM

LEFT ATRIUM

RIGHT VENTRICLE

LEFT VENTRICLE

LUNGS

PULMONARY HYPERTENSION

CONSTRICTION OF
PULMONARY ARTERIES

ENLARGED
RIGHT VENTRICLE

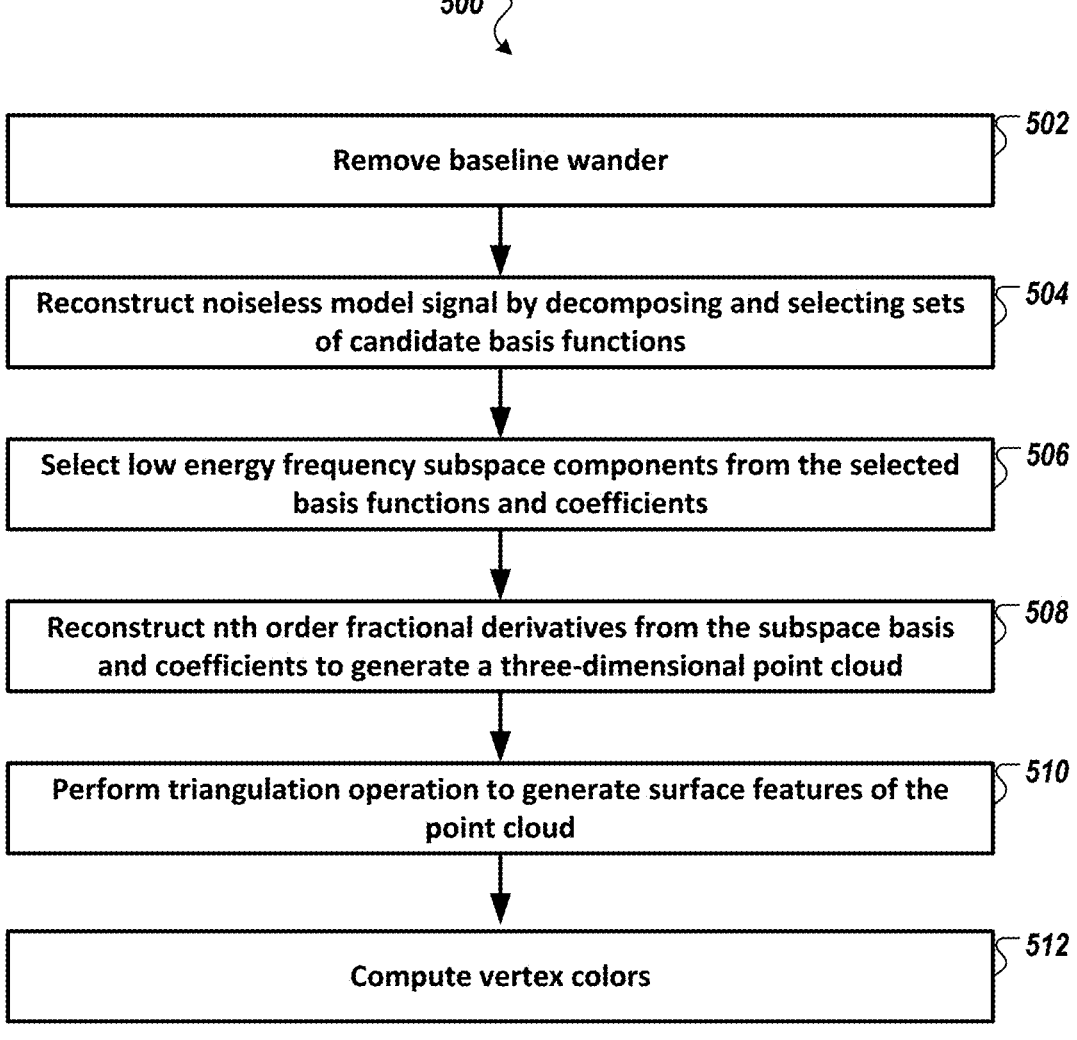

500

Remove baseline wander    502

Reconstruct noiseless model signal by decomposing and selecting sets of candidate basis functions    504

Select low energy frequency subspace components from the selected basis functions and coefficients    506

Reconstruct nth order fractional derivatives from the subspace basis and coefficients to generate a three-dimensional point cloud    508

Perform triangulation operation to generate surface features of the point cloud    510

Compute vertex colors    512

*FIG. 5*

METHOD AND SYSTEM TO ASSESS PULMONARY HYPERTENSION USING PHASE SPACE TOMOGRAPHY AND MACHINE LEARNING

RELATED APPLICATION

This application is a continuation of U.S. patent application Ser. No. 16/429,593, filed Jun. 3, 2019, entitled "Method and System to Assess Pulmonary Hypertension Using Phase Space Tomography and Machine Learning", which claims priority to, and the benefit of, U.S. Provisional Application No. 62/680,275, filed Jun. 4, 2018, entitled "Method and System to Assess Pulmonary Arterial Hypertension (PAH) Using Phase Space Tomography and Machine Learning." Both of which are incorporated by reference herein in their entireties.

FIELD OF THE DISCLOSURE

The present disclosure generally relates to non-invasive methods and systems for identifying pulmonary hypertension, including pulmonary arterial hypertension (PAH). More specifically, the present disclosure relates to non-invasive methods that utilize phase space data to generate mathematical features and phase space tomographic images, in particular, to be used in the determination of pulmonary hypertension, among other diseases and pathologies.

BACKGROUND

Pulmonary Arterial Hypertension (PAH) is a chronic and currently incurable disease that, among other things, causes the walls of the arteries of the lungs to tighten and stiffen. PAH requires at a minimum a heart catheterization for diagnosis. PAH is characterized by vasculopathy of the pulmonary arteries and defined, at cardiac catheterization, as a mean pulmonary artery pressure of 25 mm Hg or more. One form of pulmonary arterial hypertension is known as idiopathic pulmonary arterial hypertension—PAH that occurs without a clear cause. Among others, subcategories of PAH include heritable PAH, drug and toxin induced PAH, and PAH associated with other systemic diseases such as, e.g., connective tissue disease, HIV infection, portal hypertension, and congenital heart disease. PAH includes all causes that lead to the structural narrowing of the pulmonary vessels. The World Health Organization (WHO) has classified PAH as one of five groups or types of a disease state referred to as pulmonary hypertension (PH).

Pulmonary Arterial Hypertension is a sub-class of pulmonary hypertension (PH), which generally refers to high blood pressure in the arteries of the lungs and can include a spectrum of conditions. PH typically has a complex and multifactorial etiology and an insidious clinical onset with varying severity. PH may progress to complications such as right heart failure and in many cases is fatal. In addition to PAH discussed above, PH also has four other sub-classes as classified by the WHO.

The second PH group as classified by the WHO is pulmonary hypertension due to left heart disease. This group of disorders is generally characterized by problems with the left side of the heart. Such problems can, over time, lead to changes within the pulmonary arteries. Specific subgroups include left ventricular systolic dysfunction, left ventricular diastolic dysfunction, valvular disease and, finally, congenital cardiomyopathies and obstructions not due to valvular disease. Treatments of this second PH group tends to focus on the underlying problems (e.g., surgery to replace a heart valve, various medications, etc.).

The third PH group as classified by the WHO is large and diverse, generally relating to lung disease or hypoxia. Subgroups include chronic obstructive pulmonary disease, interstitial lung disease, sleep breathing disorders, alveolar hypoventilation disorders, chronic high altitude exposure, and developmental lung disease.

The fourth PH group is classified by the WHO as chronic thromboembolic pulmonary hypertension, caused when blood clots enter or form within the lungs, blocking the flow of blood through the pulmonary arteries.

Finally, the fifth PH group is classified by the WHO as including rare disorders that lead to PH, such as hematologic disorders, systemic disorders such as sarcoidosis that have lung involvement, metabolic disorders, and a subgroup of other diseases. The mechanisms of PH in this fifth group are poorly understood.

PH in all of its forms can be difficult to diagnose in a routine medical examination because the most common symptoms of PH (shortness of breath, fatigue, chest pain, edema, heart palpitations, dizziness) are associated with so many other conditions. Blood tests, chest x-rays, electro- and echocardiograms, pulmonary function tests, exercise tolerance tests, and nuclear scans are all used variously to help a physician to diagnose PH in its specific form. As noted above, the "gold standard" for PH, and for PAH in particular, is a cardiac catherization of the right side of the heart by directly measuring the pressure in the pulmonary arteries.

While the present disclosure focuses on methods and systems that facilitate the diagnosis of PAH, it is understood that insight into all forms of PH may be realized by the teachings herein.

FIGS. 1A and 1B show the differences between a subject with a normal heart (FIG. 1A) and a subject with PAH (FIG. 1B). With PAH, progressive narrowing of the pulmonary arterial bed results from an imbalance of vasoactive mediators, including prostacyclin, nitric oxide, and endothelin-1. This leads to an increased right ventricular afterload, right heart failure, and premature death.

If PAH is suspected in a subject, one of several investigations may be performed to confirm the condition, such as electrocardiography, chest radiography, and pulmonary function tests, among others. Evidence of right heart strain on electrocardiography and prominent pulmonary arteries or cardiomegaly on chest radiography is typically seen. However, a normal electrocardiograph and chest radiograph cannot necessarily exclude a diagnosis of PAH. Further tests may be needed to confirm the diagnosis and to establish cause and severity. For example, blood tests, exercise tests, and overnight oximetry tests may be performed. Yet further, Imaging testing may also be performed. Imaging testing examples include isotope perfusion lung scanning, high resolution computed tomography, computed tomography pulmonary angiography, and magnetic resonance pulmonary angiography.

If these (and possibly other) non-invasive investigations support a diagnosis of PAH, right heart catheterization typically is needed to confirm the diagnosis by directly measuring pulmonary pressure. It also allows measurement of cardiac output and estimation of left atrial pressure using pulmonary arterial wedge pressure.

While non-invasive techniques exist to determine PAH may exist in a subject, these techniques cannot reliably confirm a diagnosis of PAH unless an invasive right heart catherization is performed. The current state of the art fails to provide for techniques that can facilitate an accurate diagnosis of PAH through modeling and analysis.

SUMMARY

The exemplified intrinsic phase space tomography methods and systems facilitate the analysis and evaluation of complex, quasi-periodic system by generating tomographic images and mathematical features as a representation of the dynamics of the quasi-periodic cardiac systems. Indeed, electrical conduction patterns of the heart, or other acquired biophysical signals of other organs, can be represented as phase space tomographic images generated as views of a phase space volumetric object (also referred to as a phase space model) that has both a volumetric structure (e.g., a three-dimensional structure) and/or a color map. In some implementations, the phase space tomographic images are presented as two-dimensional views of the phase space volumetric object to assist a physician in the assessment of the presence or non-presence of disease. In other implementations, the phase space tomographic image is presented as a three-dimensional representation of the phase space volumetric object. In other implementations, mathematical features are calculated that represent elements of the phase space. In some implementations, the phase space tomographic images are used as input to a trained neural network classifier configured to assess for the presence or non-presence of pulmonary arterial hypertension. The phase space tomographic images and outputs of the classifier can be presented to a physician to assist in the assessment of the presence or non-presence of disease. In some implementations, the mathematical features are used as input to a trained neural network classifier configured to assess for presence or non-presence of pulmonary arterial hypertension. The outputs of the classifier can be presented to a physician to assist in the assessment of presence or non-presence of disease. The exemplified methods and systems represents a new and efficient technique of assessing the presence of pulmonary arterial hypertension, among other diseases and pathologies.

In an aspect, a method is disclosed for non-invasively assessing presence or non-presence of pulmonary hypertension. The method includes obtaining, by one or more processors (e.g., from a stored database or from a measurement equipment), acquired data from a measurement of one more biophysical signals of a subject (e.g., biopotential-based signals, ultrasound-based signals, magnetic-based signals), wherein the acquired data is derived from measurements acquired via noninvasive equipment configured to measure properties (e.g., electric properties, magnetic properties, acoustic properties, impedance properties, and etc.) of the heart; and generating, by the one or more processors, a set of tomographic images derived from a phase space model generated based on the acquired data, wherein at least one of the phase space model comprises a plurality of faces and a plurality of vertices, wherein the plurality of vertices are defined, in part, by fractional subspace derivative operations of low-energy subspace parameters generated directly or indirectly from the acquired data; wherein the set of tomographic images are presented (e.g., on a local or a remote computing system) for an assessment of presence and/or non-presence of pulmonary hypertension.

In some embodiments, the method includes determining, by the one or more processors, a machine-trained assessment of presence and/or non-presence of pulmonary hypertension using a trained neural network-based nonlinear classifier (e.g., wherein the classifier is configured to map individual pixels of the tomographic images to a binary predictor).

In some embodiments, the method includes generating a contour data set for each tomographic image of the set of tomographic images, wherein the contour data are presented for the assessment of presence and/or non-presence of pulmonary hypertension.

In some embodiments, the contour data set is generated by sweeping, via the one or more processors, a moving window associated with the trained neural network-based nonlinear classifier on a pixel by pixel basis over, at least a portion of, a given tomographic image; and combining, for a given pixel of the tomographic image, outputs of the swept moving window.

In some embodiments, the method includes presenting, via a display of a remote computing system, the generated contour data set (e.g., as an overlay over a rendering of the machine-trained assessment or as an overlay over the set of tomographic images).

In some embodiments, the method includes presenting, via the display of the remote computing system, the generated contour data set and a corresponding tomographic image used to generate the contour data set, wherein the generated contour data set is rendered as an overlay over the corresponding tomographic image.

In some embodiments, the generated contour data set comprises color map data.

In some embodiments, the method includes presenting, via a display of the remote computing system, the set of tomographic images in conjunction with the generated contour data set.

In some embodiments, the vertices and faces of the generated phase space model comprises color data, the steps of generating the tomographic images comprising converting the generated phase space model to greyscale.

In some embodiments, the tomographic images are generated by generating a plurality of images corresponding to a plurality of orientation of the generated phase space model, wherein the image is generated at a first image resolution; and converting the plurality of images to a second image resolution, wherein the second image resolution is different from the first image resolution (e.g., wherein the second image resolution has a lower number of pixels as compared to the first image resolution).

In some embodiments, the method includes determining, by the one or more processors, one or more coronary physiological parameters of the subject selected from the group consisting of a fractional flow reserve estimation, a stenosis value, and a myocardial ischemia estimation, based on the generated phase space model (e.g., and causing, by the one or more processors, output of the one or more coronary physiological parameters (e.g., in a report, a display, instrumentation output, etc.)).

In some embodiments, the generated phase space model comprises a three-dimensional object defined by the plurality of faces and a plurality of vertices.

In some embodiments, the plurality of vertices are generated as a point cloud in 3D space (e.g., having X, Y, and Z components), wherein each point in the point cloud is associated with a fractional order of a fractional subspace derivative operation of the low-energy subspace parameters (e.g., wherein a fractional subspace derivative operation of the low-energy subspace parameters for a given fractional order generates a 2D data set).

In some embodiments, each fractional order of the fractional subspace derivative operation is predetermined.

In some embodiments, each of the plurality of vertices comprises one or more attribute parameters (e.g., color).

In some embodiments, each of the plurality of vertices comprises one or more color attribute parameters.

In some embodiments, at least one of the one or more color attribute parameters is associated with a variance of a modeled channel signal generated from a model-derived construction (e.g., a sparse approximation algorithm such as, or based on, principal component analysis (PCA), matching pursuit, orthogonal matching pursuit, orthogonal search, projection pursuit, LASSO, fast orthogonal search, Sparse Karhunen-Loeve Transform, and combinations thereof) of the acquired data subtracted from a baseline-removed raw channel of the acquired data.

In some embodiments, the plurality of faces are generated from a triangulation operation of the plurality of vertices.

In some embodiments, the plurality of faces are generated from the triangulation operation, the triangulation operation being selected from the group consisting of Delaunay triangulation, Mesh generation, Alpha Hull triangulation, and Convex Hull triangulation.

In some embodiments, each of the plurality of faces comprises one or more face attribute parameters (e.g., color).

In some embodiments, each of the plurality of faces comprises one or more face color attribute parameters.

In some embodiments, at least one of the one or more face color attribute parameters is a triangular interpolation among bounding vertex attribute parameters (e.g., 3 bound vertex colors).

In some embodiments, the fractional order is a rational number or an irrational number associated with one or more linear and/or non-linear dynamic response of the heart.

In some embodiments, the method further includes removing, by the one or more processors, a baseline wandering trend from the acquired data prior to generating the one or more phase space models.

In some embodiments, the method further includes performing a model-derive reconstruction operation of the acquired data to generate the low-energy subspace parameters, the low-energy subspace parameters comprising a plurality of basis functions and coefficients (e.g., a linear combination of plurality of basis functions scaled by one or more coefficients).

In some embodiments, the low-energy subspace parameters consist of low-energy subsets of plurality of basis functions and coefficients.

In some embodiments, the low-energy subsets of plurality of basis functions and coefficients are selected from the group consisting of: about 1% of plurality of basis functions and coefficients associated with low energy frequency subspace; about 5% of plurality of basis functions and coefficients associated with low energy frequency subspace; about 10% of plurality of basis functions and coefficients associated with low energy frequency subspace; about 15% of plurality of basis functions and coefficients associated with low energy frequency subspace; about 20% of plurality of basis functions and coefficients associated with low energy frequency subspace; and about 25% of plurality of basis functions and coefficients associated with low energy frequency subspace.

In some embodiments, the model-derived reconstruction operation generates over 100 basis functions and coefficients for a given acquired data.

In some embodiments, parameters associated with generated one or more phase space models are used in subsequent machine learning operations (e.g., image-based machine learning operations or feature-based machine learning operations) to determine the one or more coronary physiological parameters.

In some embodiments, parameters associated with generated one or more phase space models are associated with geometric properties of the generated one or more phase space models.

In some embodiments, the parameters associated with generated one or more phase space models are associated with geometric properties of the generated one or more phase space models selected from the group consisting of volume, number of distinct bodies, and color gradient.

In some embodiments, the method includes causing, by the one or more processors, generation of a visualization of generated phase space volumetric object as a three-dimensional object, wherein the three-dimensional object is rendered and displayed at a display of a computing device (e.g., computing workstation; a surgical, diagnostic, or instrumentation equipment).

In some embodiments, the method includes causing, by the one or more processors, generation of a visualization of generated phase space model as a three-dimensional object, wherein the three-dimensional object is displayed in a report (e.g., an electronic report).

In some embodiments, the acquired data comprises differential channel signals (e.g., 3 sets of differential measurement simultaneously sampled; or 6 sets of unipolar measurements simultaneously sampled).

In some embodiments, the acquired data comprise signals associated with interference (e.g., in phase plane) of depolarization waves among orthogonal leads.

In some embodiments, the method further includes extracting a first set of morphologic features of the generated phase space model, wherein the first set of extracted morphologic features include parameters selected from the group consisting of a 3D volume value, a void volume value, a surface area value, a principal curvature direction value, and a Betti number value.

In some embodiments, the method further includes dividing the generated phase space model into a plurality of segments each comprising non-overlapping portions of the generated phase space model; and extracting a set of morphologic features of each of the plurality of segments, wherein the second set of extracted morphologic features includes parameters selected from the group consisting of a 3D volume value, a void volume value, a surface area value, a principal curvature direction value, and a Betti number value.

In some embodiments, the plurality of segments comprise a number of segments selected from the group consisting of 3, 4, 5, 6, 7, 8, 9, 10, 11, 12, 13, 14, 15, 16, 17, 18, 19, and 20.

In some embodiments, the acquired data are acquired as one or more wide-band gradient signals simultaneously from the subject via at least one electrode.

In some embodiments, at least one of one or more wide-band gradient signals comprise a high-frequency time series data that is unfiltered (e.g., spectrally unmodified) prior to the processing in the phase-space analysis.

In some embodiments, the one or more wide-band gradient signals comprise cardiac frequency information at a frequency selected from the group consisting of about 1 kHz, about 2 kHz, about 3 kHz, about 4 kHz, about 5 kHz, about 6 kHz, about 7 kHz, about 8 kHz, about 9 kHz, about 10 kHz, and greater than 10 kHz (e.g., 0-50 kHz or 0-500 kHz).

In another aspect, a system is disclosed comprising a processor and a memory having instructions thereon, wherein the instructions, when executed by the processor, cause the processor to perform any of the above-referenced methods.

In another aspect, a non-transitory computer readable medium is disclosed having instructions stored thereon, wherein execution of the instructions cause the processor to perform any of the above-referenced methods.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

Implementations of the present disclosure may be better understood from the following detailed description when read in conjunction with the accompanying drawings. Such implementations, which are for illustrative purposes only, depict novel and non-obvious aspects of the disclosure. The drawings include the following figures:

FIG. 5 is an example method of generating a phase space volumetric object by the non-invasive cardiac assessment system in accordance with an illustrative implementation;

DETAILED SPECIFICATION

Each and every feature described herein, and each and every combination of two or more of such features, is included within the scope of the present disclosure provided that the features included in such a combination are not mutually inconsistent.

Figure 2:
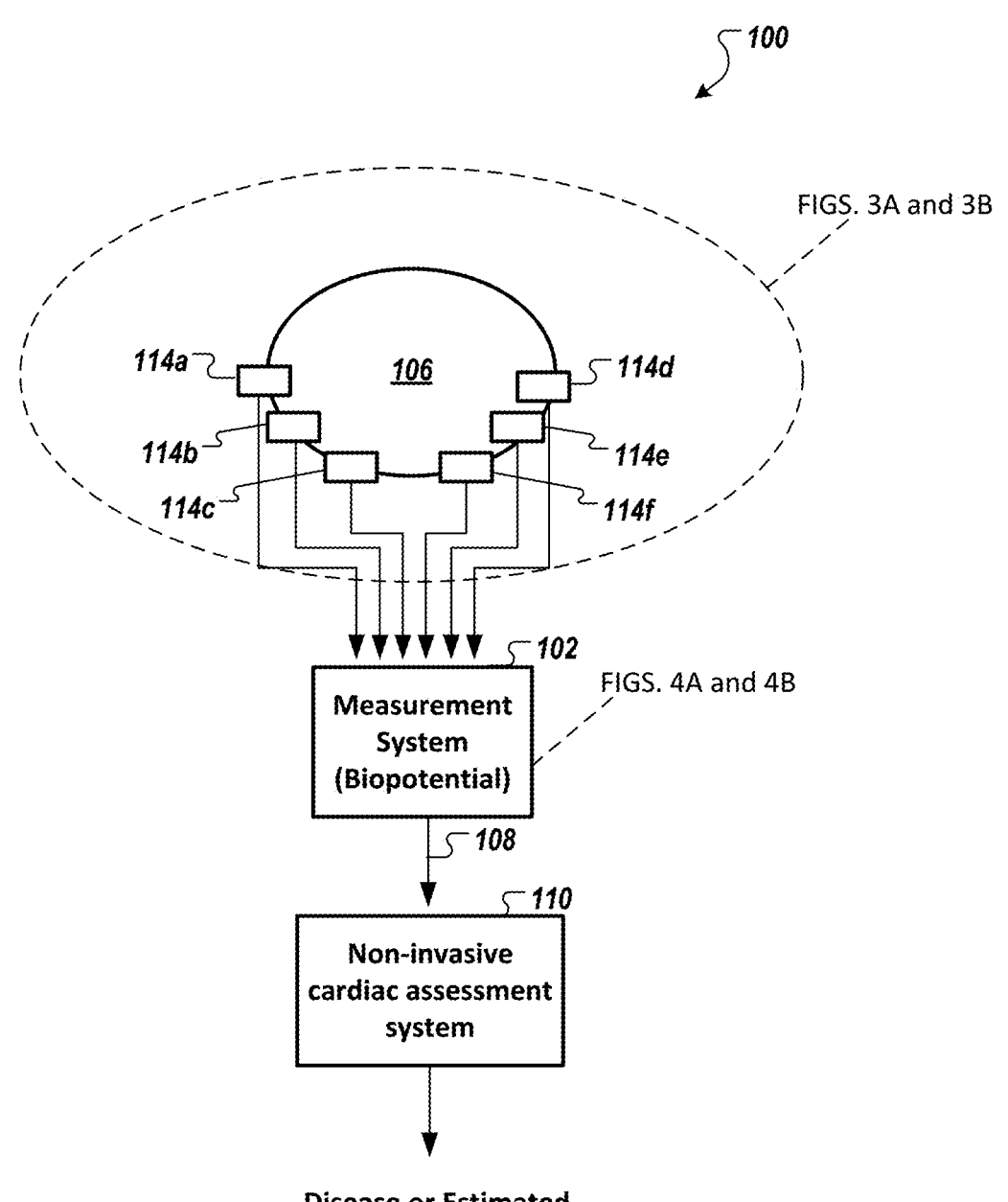
FIG. 2 is a diagram of an example system configured to assess non-invasively presence or non-presence of pulmonary arterial hypertension using cardiac phase gradient computed tomographic images, in accordance with an illustrative implementation.

FIG. 2 is a diagram of an example system 100 configured to assess non-invasively presence or non-presence of pulmonary arterial hypertension using cardiac phase gradient computed tomographic images, in accordance with an illustrative implementation.

Figure 3A:
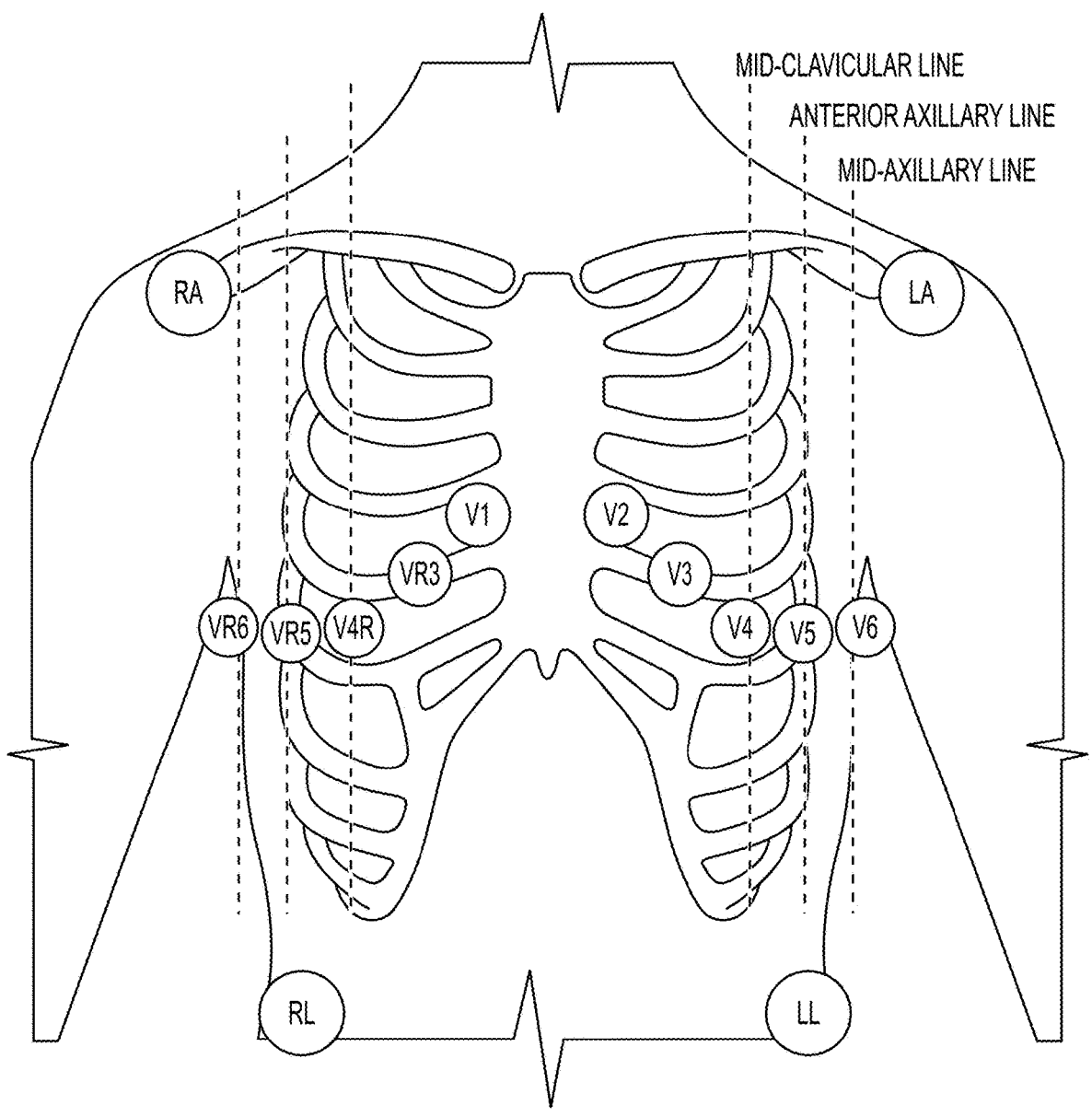
FIGS. 3A and 3B illustrate example lead placement locations in accordance with the present disclosure.
Figure 3A:
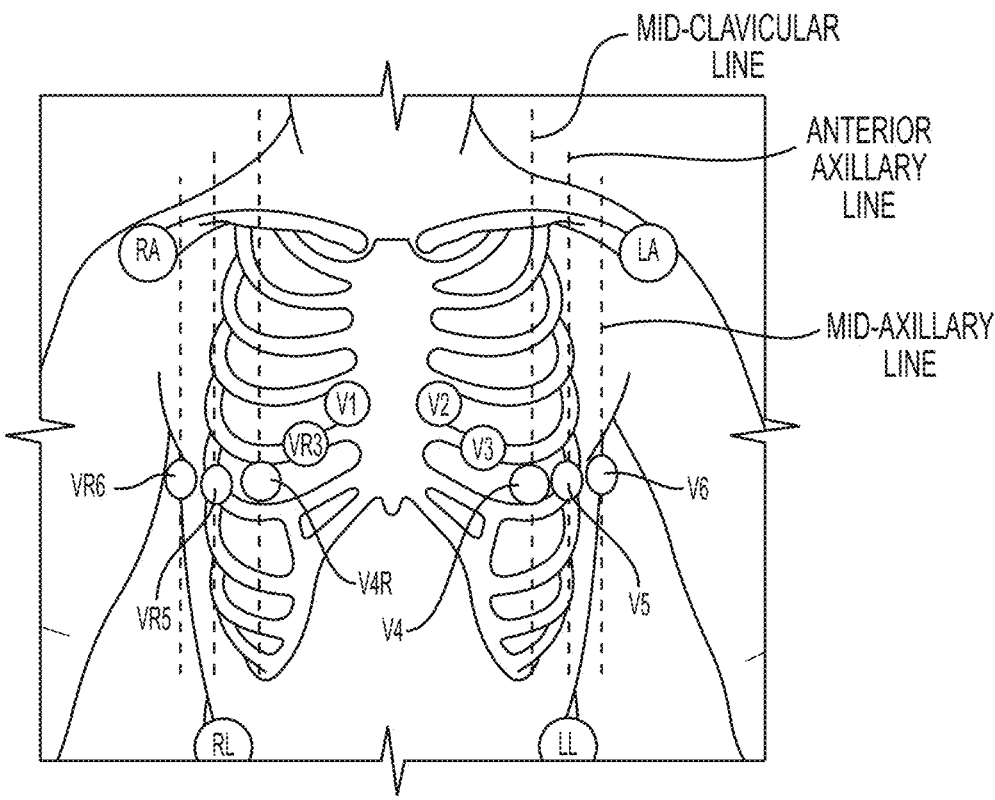
Figure 3B:
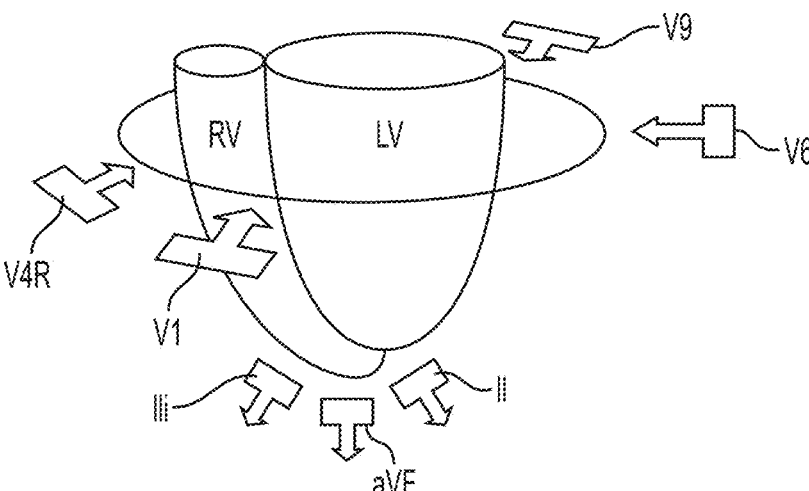

In FIG. 2, a non-invasive measurement system 102 acquires a plurality of biophysical signals 104 (e.g., phase gradient biopotential signals) via probes 114 (shown as probes 114a, 114b, 114c, 114d, 114e, and 114f) from a subject 106 to produce a phase-gradient biophysical data set 108. More detail of the placement of the probes 114a-114f is shown in FIGS. 3A and 3B, which shows an arrangement of three axes, focused on the left side of the heart. Other arrangements may be used to provide greater visibility of the right side of the heart.

An assessment system 110 (shown as "non-invasive cardiac assessment system" 110) receives the phase-gradient biophysical data set 108 and generates one or more phase space volumetric objects 112a/b (shown in FIGS. 4A and 4B; also referred to herein as a "phase space volumetric model") and mathematical features for analysis of the phase-gradient biophysical data set 108. Each of the phase space volumetric objects 112a/b as a three-dimensional structure includes a plurality of vertices generated as a point cloud in three-dimensional space and a plurality of faces defined by the plurality of vertices. As will be described herein, the input data set 108 has a shape and the shape has a meaning; i.e., the shape is indicative of a condition such as PAH.

The assessment system 110 can further determine, in some implementations, a set of computed phase space tomographic images from the phase space volumetric objects 112. A machine learned classifier can be applied on the computed phase space tomographic images or the computed phase space tomographic images from which the images are derived to assess the contextual information on cardiac health. The color and shape of the phase space volumetric objects 112a/b and computed phase space tomographic images derived therefrom beneficially synthesize and display the electrical and functional characteristics of the heart.

Each, or a substantial portion, of the plurality of vertices of the phase space volumetric objects 112a/b corresponds to a fractional order derivative operation as applied, for example, to a subspace data set (e.g., a low-energy frequency subspace data set) of a three-dimensional phase space model generated from the phase-gradient biophysical data set 108. The three-dimensional phase space model can be configured as a set of time series data of three sets of differential channel signals derived from the phase-gradient biophysical data set 108. The fractional derivative operations can be used, for instance, to compensate for noise, lead placement errors and to create more accurate tissue impedance models.

The phase space volumetric objects 112a/b include a plurality of faces generated by a triangulation operation on the three-dimensional point cloud. In some implementations, the triangulation operation includes an Alpha Hull triangulation operation of the three-dimensional time-series points in which a predetermined radius a is used to generate faces that are mapped to the plurality of vertices. In other implementations, Delaunay triangulation, alpha shapes, ball pivoting, Mesh generation, Convex Hull triangulation, and the like, is used.

As discussed in U.S. Publication No. 2013/0096394, which is incorporated by reference herein in its entirety, a mathematical reconstruction of the phase-gradient biophysical data signal may comprise various elements including, in some implementations, an input/output (I/O) expansion of the phase-gradient biophysical data signal in which at least one of the terms of the I/O expansion are fractionally differentiable (e.g., analytically fractionally differentiable). In some implementations, the I/O expansion comprises a fractional integral of the mathematical reconstruction. Sparse approximation operation comprises a set of operations, often iterative, to find a best matching projection of a data set (e.g., multi-dimensional data) onto candidate functions in a dictionary. Each dictionary can be a family of waveforms that is used to decompose the input data set. The candidate functions, in some implementations, are linearly combined to form a sparse representation of the input data set. These operations can be numerical or analytical. In some implementations, the mathematical reconstruction is based on principal component analysis (PCA), matching pursuit, orthogonal matching pursuit, orthogonal search, projection pursuit, LASSO, fast orthogonal search, Sparse Karhunen-Loeve Transform, or combinations thereof. In other implementations, the I/O expansion comprises an irrational fractional subspace derivative of the mathematical reconstruction of the phase-gradient biophysical data signal. The recited examples are not exhaustive and other sparse approximation algorithms or methods may be used as well as any variations and combinations thereof.

As discussed in U.S. Publication No. 2013/0096394, there are a couple of points about the low-energy component subspace (made from the last, e.g., 20% terms found by a matching pursuit reconstruction algorithm operation) that are interesting and useful. First, the fractional integral and derivative of these components can be noiselessly determined, since it is a linear combination of selected candidate terms, and this fractional derivative can be useful to distinguish ventricular tachycardia potential in post myocardial infarction patients and those with congenital heart defects. In addition, there are some useful fractional properties to consider. Thus, suppose that x(t), y(t), and z(t) are respectively the X, Y, and Z coordinates of the low-energy component and let $x_a(t)$, $y_a(t)$, and $z_a(t)$ be their irrational fractional derivative of order a that can be any real or complex number.

To predict presence or non-presence of pulmonary arterial hypertension from the phase-space tomographic images, a trained neural network is applied, in some implementations, to a number of views (e.g., six views) of each tomographic image (e.g., top, bottom, front, back, left and right view). In some implementations, images acquired of the three-dimensional volumetric object 112a/b are first converted to grayscale and then scaled to a pre-defined image resolution (e.g., 195×128 pixels). Other pixel count and image resolution formats can be used. In some implementations, the neural network classifier includes multiple hidden neurons (e.g., 15 hidden neurons) with leaky rectified linear activations. Dropout may be used between the hidden layer and the final output neuron to prevent overfitting. L1 and L2 regularization penalties may also be applied. A binary cross entropy may be used as a loss function. Optimization may be performed using the gradient-based Adam algorithm.

Heat maps and contour plots, in some implementations, are generated from the outputs of the neural network classifier on a given phase-space tomographic image or from the computed phase space tomographic images themselves. In some implementations, a 4×4 moving window of white pixels (e.g., having a value of 1 in grayscale images) is swept over the entire image, with the neural network classifier being evaluated once for each window position and the output of the neural network being recorded. When a given pixel in the PST image is covered by the moving window more than once (e.g., when the window is larger than a single pixel but moving one pixel at a time), each pixel in the heat map may have a value that is an average output of the neural network classifier when the corresponding pixel in the phase-space tomographic image is covered by the window. Contour plots may be generated using the same data as the heat maps.

Figure 4A:
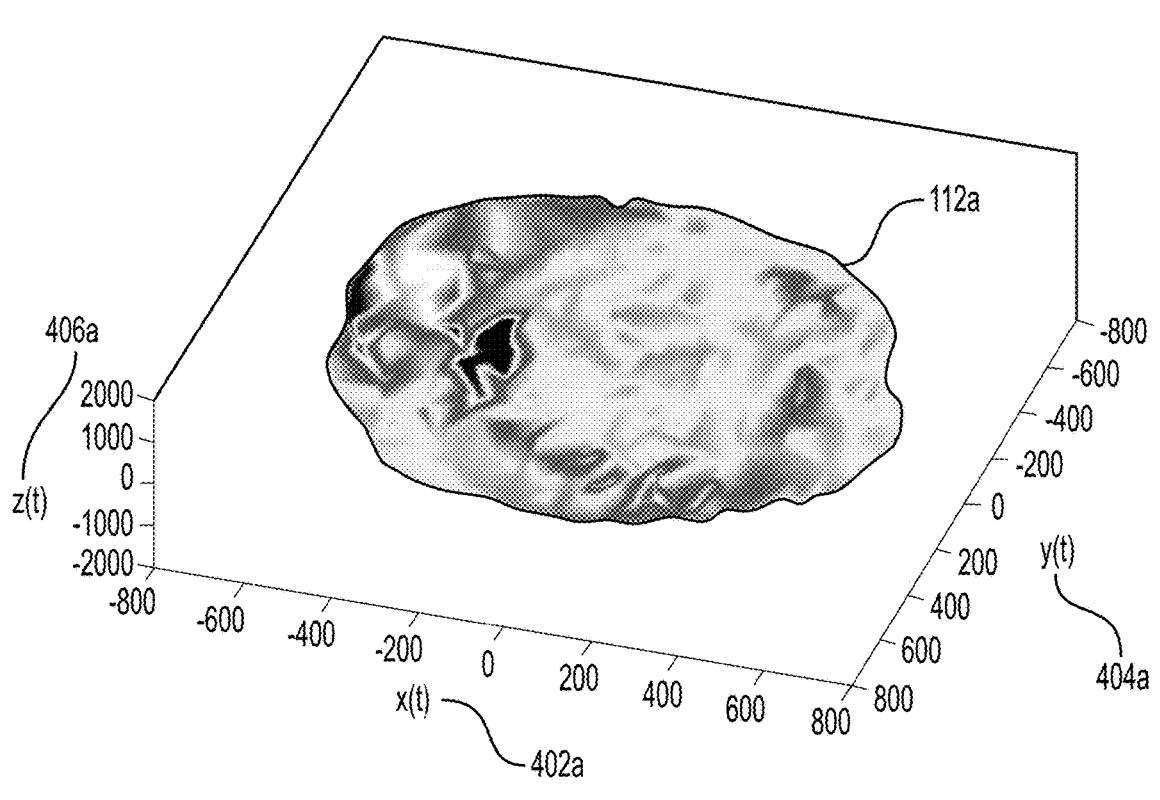
FIGS. 4A and 4B each shows a phase space volumetric object generated from a biophysical measurement of a subject determined to have pulmonary arterial hypertension in accordance with an illustrative implementation.
Figure 4B:
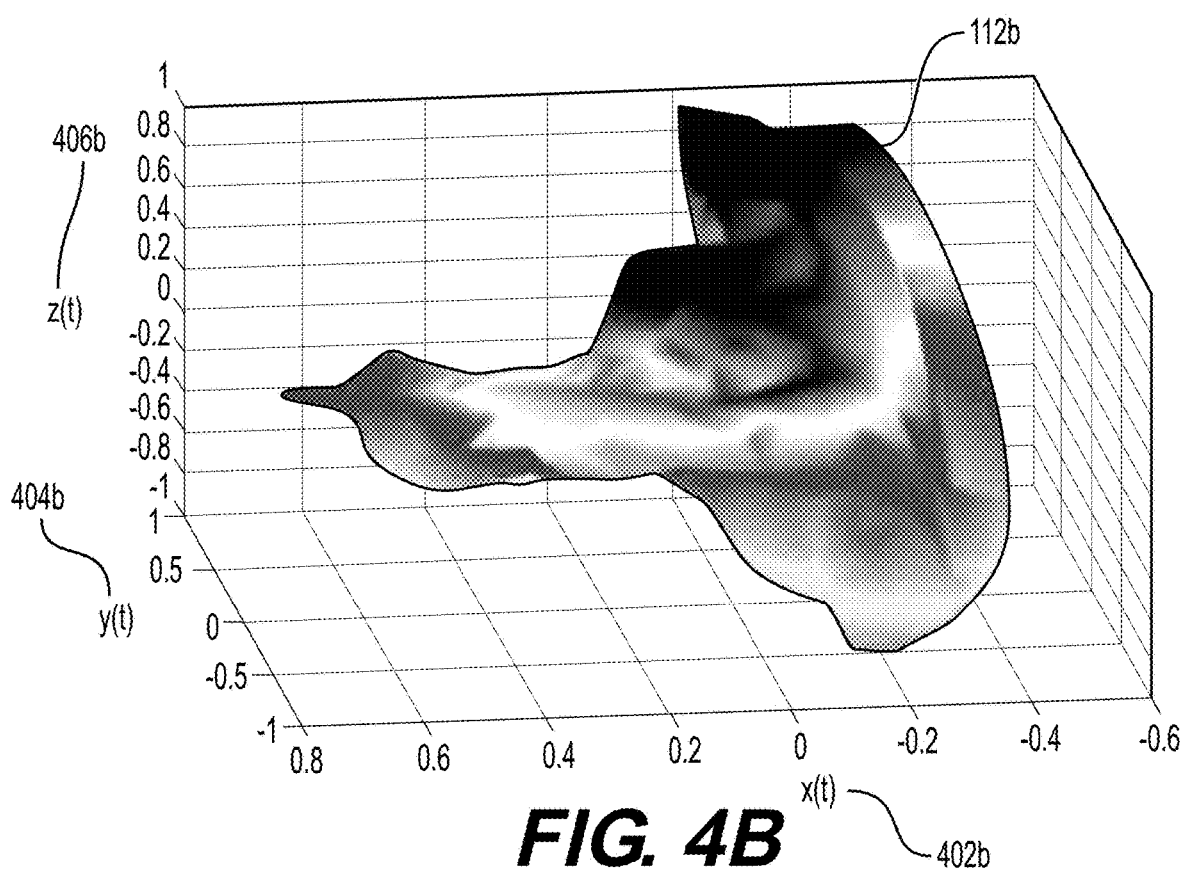

Given that computed phase space tomographic images 112a/b are rendered images of the phase space volumetric object from a specific vantage and/or view, a phase space volumetric object can also be referred to as a computed phase space tomographic image. As shown in FIGS. 4A and 4B, each of the x-axis 402a/b, y-axis 404a/b, and z-axis 406a/b of the phase space volumetric object includes a set of fractional derivative orders associated with fractional derivative operations performed on components of a subspace data set. The fractional derivative operation non-linearly preserves and enhances features of the subspace data set in different frequency bands. To this end, long cardiac phase gradient signals, existing as high-dimensional data due to the multiple acquisition leads, and exhibiting complex nonlinear variability, can be efficiently captured by this modeling techniques.

The set of fractional derivative orders in FIGS. 4A and 4B include orders in a sequence of ascending or descending values that are equally spaced apart from one another along each respective axis (402a/b, 404a/b, 406a/b). In some implementations, the fractional derivative orders are pre-defined and correspond to frequencies of electrical conduction events of the heart including those associated with activation (e.g., ventricular and/or atrio depolarization) of the various chambers and recovery (i.e., ventricular and/or atrio repolarization).

Indeed, the phase space volumetric object 112a/b provides a framework of aggregating multiple analyses (i.e., fractional derivative transform) of subspace data set that non-linearly preserves and enhances features in the low-energy frequency subspace data set in different frequency bands and representing these analyses, and/or the results thereof, as a three-dimensional volumetric object. In addition to being visually more distinct when rendered, it is observed that various topologic or geometric characteristics of the phase space volumetric object 112a/b can be readily extracted and/or determined to be used as predictors of presence or non-presence of pulmonary arterial hypertension. In some implementations, the extracted topologic or geometric characteristics include an assessed volume of the phase space volumetric object 112. In other implementations, views of the phase space volumetric object can be presented as computed tomographic images that can be directly presented to a physician for evaluation.

In some implementations, different fractional derivative orders may be used for different axes of the phase space model. In some implementations, inputs from different sensor types may be fused in a single-phase space model to which different sets of fractional derivative orders may be applied for each respective sensor type.

In some implementations, the set of fractional derivative orders include at least 5 orders (i.e., frequencies). In some implementations, the set of fractional derivative orders include at least 10 orders (i.e., frequencies). In some implementations, the set of fractional derivative orders include at least 20 orders. In some implementations, the set of fractional derivative orders include at least 30 orders. In some implementations, the set of fractional derivative orders include at least 40 orders. In some implementations, the set of fractional derivative orders include at least 50 orders. In some implementations, the set of fractional derivative orders include more than 50 orders. These frequency bands can be between about 0.01 Hz and about 10 Hz in some implementations. In other implementations, the frequency bands are between about 0.01 Hz and about 100 Hz. In some implementations, the frequency bands are between about 0.01 Hz and about 1000 Hz. In other implementations, the frequency bands are between about 0.01 Hz and about 10,000 Hz. In other implementations, the frequency bands have a maximum value that extend beyond 10,000 Hz.

As shown in FIGS. 4A and 4B, in addition to structural components, in some implementations, the phase space volumetric object 112*a/b* is configured with color map information that corresponds to additional dimension of analysis. In some implementations, each vertex has one or more color values that are calculated as a variance between a modeled channel data set (e.g., X-axis data set, Y-axis data set, or Z-axis data set) a base-line raw channel data set (e.g., corresponding X-axis data set, Y-axis data set, or Z-axis data set). In some implementations, the variance is determined by subtracting data points of the base-line raw channel data set with the corresponding data points of the modeled channel data set. The modeled channel data set, in some implementations, is based on a sparse approximation of the base-line raw channel data set to generate a reconstructed noiseless signal of the base-line raw channel data. In some implementations, each face of the phase space volumetric object 112*a/b* is assigned a face color value triangularly interpolated among neighboring bounding vertex color values (e.g., 3 bounding vertex colors).

Example Method to Construct a Phase Space Volumetric Object

FIG. 5 is an example method 500 of generating a phase space volumetric object 112*a/b* by the non-invasive cardiac assessment system 110 in accordance with an implementation of the present disclosure. Other implementations may become evident to one of ordinary skill in the art based on this disclosure. The method 500 includes removing (operation 502) a baseline wander from the raw differential channel signal of phase-gradient biophysical data set 108. In some implementations, the raw differential channel signal is derived from six signals simultaneously sampled by the measurement system 102.

In some implementations, six simultaneously sampled signals are captured from a resting subject as the raw differential channel signal data set in which the signals embed the inter-lead timing and phase information of the acquired signals, specific to the subject. Geometrical contrast arising from the interference in the phase plane of the depolarization wave with the other orthogonal leads can be used which can facilitate superimposition of phase space information on a three-dimensional representation of the heart. Noiseless subspaces further facilitate the observation of the phase of these waves. That is, the phase of the orthogonal leads carries the information about the structure and generates geometrical contrast in the image. Phase-contrast takes advantage of the fact that different bioelectric structures have different impedances, and so spectral and non-spectral conduction delays and bends the trajectory of phase space orbit through the heart by different amounts. These small changes in trajectory can be normalized and quantified beat to beat and corrected for abnormal or poor lead placement, and the normalized phase space integrals can be mapped to a geometric mesh for visualization.

In some implementations, the raw differential channel signal data set are normalized and baseline wander removed using a modified moving average filter. For example, in some implementations, the baseline wander is extracted from each of the raw differential channel signals using a median filter with an order of 1500 milliseconds, smoothed with a 1-Hz low-pass filter, and subtracted from the signals. The bias is then removed from the resulting signals by subtracting estimations of the signals using maximums of probability densities calculated with a kernel smoothing function. All of the signals may be divided by their respective interquartile ranges to complete the normalization process.

The method 500 then includes reconstructing (operation 504) a noiseless model signal by decomposing and selecting sets of candidate basis functions to create a sparse mathematical model. In some implementations, a Modified Matching Pursuit (MMP) algorithm is used to find a noiseless model of the raw differential channel signals. Other sparse approximation algorithms can be used, including, and not limited to, evolvable mathematical models, symbolic regression, orthogonal matching pursuit, LASSO, linear models optimized using cyclical coordinate descent, orthogonal search, fast orthogonal search, and cyclical coordinate descent. In some implementations, the reconstructing operation 504 generates a model as a function with a weighted sum of basis functions in which basis function terms are sequentially appends to an initially empty basis to approximate a target function while reducing the approximation error.

The method 500 then includes selecting (operation 506) subspace components (e.g., low energy frequency subspace components) from the selected basis functions and coefficients. The low-energy subspace components comprise a model reconstructed by using only the X % low magnitude subset coefficients (frequency content) contributing least to the modelling error. Low-energy subspace components, in some implementations, includes higher order candidate terms that are later selected, in the phase space coordinates, as part of the sparse representation of a signal. That is, the last 5 percent, 10 percent, 15 percent, 20 percent, 25 percent, 30 percent of the candidate terms (as the higher order candidate terms) last selected via the sparse approximation is used. Other percentage values can be used.

The method 500 then includes reconstructing (operation 508) a pre-defined set of $n^{th}$ order fractional derivative result set (e.g., via a numeric fractional derivative operation) to generate a three-dimensional point cloud defining, in part, the phase space volumetric object 112. In some implementations, the fractional derivative operation is based on Grunwald-Letnikov fractional derivative method. In some implementations, the fractional derivative operation is based on the Lubich's fractional linear multi-step method. In some implementations, the fractional derivative operation is based on the fractional Adams-Moulton method. In some implementations, the fractional derivative operation is based on the Riemann-Liouville fractional derivative method. In some implementations, the fractional derivative operation is based on Riesz fractional derivative method. Other methods of performing a fractional derivative may be used.

The method 500 then includes, in some implementations, performing (510) triangulation operation to generate surface features (i.e., faces) of the point cloud. In some implementations, Alpha Hull triangulation with a pre-predetermined radius ($\alpha$) is performed on the reconstructed noiseless model signals. In other implementations, Delaunay triangulation, alpha shapes, ball pivoting, Mesh generation, Convex Hull triangulation, and the like, is used.

The method 500 then includes, in some implementations, computing (512) one or more values for each of the vertices in the point cloud. The vertex values, in some implementations, are scaled over a presentable color range. The vertex values, in some implementations, are a variance between a modeled channel data set (e.g., X-axis data set, Y-axis data set, or Z-axis data set) and a base-line raw channel data set (e.g., corresponding X-axis data set, Y-axis data set, or Z-axis data set). In some implementations, the variance is determined by subtracting data points of the base-line raw channel data set with the corresponding data points of the modeled channel data set. The modeled channel data set, in some implementations, is based on a sparse approximation of the base-line raw channel data set to generate a reconstructed noiseless signal of the base-line raw channel data. In some implementations, each face of the phase space volumetric object 112a/b is assigned a face color value triangularly interpolated among neighboring bounding vertex color values (e.g., 3 bounding vertex colors).

In some implementations, various views of the phase space volumetric object 112a/b are captured for presentation as computed phase space tomographic images, e.g., via a web portal, to a physician to assist the physician in the assessment of presence or non-presence of pulmonary arterial hypertension. In some implementations, the phase space volumetric object or the computed phase space tomographic images are assessed by a trained neural network classifier configured to assess for presence or non-presence of pulmonary arterial hypertension. In some implementations, the computed tomographic images are presented alongside the results of a machine-generated predictions to assist in the physician in making a diagnosis.

In other implementations, the phase space volumetric object 112a/b is analyzed in subsequent machine learning operations (e.g., image-based machine learning operations or feature-based machine learning operations) to determine the one or more coronary physiological parameters. In some implementations, the assessment system 110 is configured to determine a volumetric (e.g., alpha hull volume) of the phase space volumetric object 112a/b. In some implementations, the assessment system 110 is configured to determine a number of distinct bodies (e.g., distinct volumes) of the generated phase space volumetric object 112a/b. In some implementations, the assessment system 110 is configured to assess a maximal color variation (e.g., color gradient) of the generated phase space volumetric object 112. In some implementations, all these features are assessed from phase space volumetric object 112a/b as a mathematical feature.

In some implementations, the mathematical features of the phase space volumetric object 112a/b are extracted along with hundreds of other distinct mathematical features that represent specific aspects of the biophysical signals collected. A feature extraction engine of the assessment system 110 may extract each feature as a specific formula/algorithm. In some implementations, when the feature extraction process is applied to an incoming biophysical signal, the output is a matrix of all calculated features which includes a list, for example, of over hundreds of real numbers; one number per feature in which each feature represents one or more aspects of the signal's dynamical, geometrical, fractional calculus, chaotic, and/or topological properties.

A machine learning algorithm (e.g., meta-genetic algorithm), in some implementations, is used to generate predictors linking aspects of the phase space model (e.g., pool of features) across a population of patients representing both positive (i.e., have disease) and negative (i.e., do not have disease) cases to detect the presence of myocardial tissue associated with pulmonary arterial hypertension. In some implementations, the performances of the candidate predictors are evaluated through a verification process against a previously unseen pool of patients. In some implementations, the machine learning algorithm invokes a meta-genetic algorithm to automatically select a subset of features drawn from a large pool. This feature subset is then used by an Adaptive Boosting (AdaBoost) algorithm to generate predictors to diagnose pulmonary arterial hypertension across a population of patients representing both positive and negative cases. The performances of the candidate predictors are determined through verification against a previously unseen pool of patients. A further description of the AdaBoost algorithm is provided in Freund, Yoav, and Robert E. Schapire, "A decision-theoretic generalization of on-line learning and an application to boosting," European conference on computational learning theory. Springer, Berlin, Heidelberg (1995), which is incorporated by reference herein in its entirety.

In some implementations, the system 100 generates one or more images of a representation of the phase space volumetric object 112a/b in which the vertices, face triangulations, and vertex colors are presented. In some implementations, multiple views of the representation are generated and included in a report. In some implementations, the one or more images are presented as a three-dimensional object that can be rotated, scaled, and/or panned based on user's inputs. Indeed, such presentation can be used to be assessed visually by a skilled operator to determine whether a subject has presence of non-presence of pulmonary arterial hypertension.

Cardiac Phase Space Tomography

As noted above, computed tomographic images that the physician can themselves interpret, can be produced based on the phase-space volumetric object. In some implementations, the phase space volumetric objects 112a/b are used to generate a set of two dimensional views as the computed phase space tomographic images which can be directly interpreted, e.g., by a physician or by a machine learned classifier to assess for presence or non-presence of pulmonary arterial hypertension.

Neural Network Classification

The three-dimensional phase-space volumetric object or the computed phase-space tomographic images can be directly evaluated by a trained neural network classifier to determine presence or non-presence of pulmonary arterial hypertension. In some implementations, the neural network classifier may be a neural network trained on a set of grayscale tomographic images which are paired with coronary angiography results assessed for presence and non-presence of pulmonary arterial hypertension. In some implementations, a neural network-based nonlinear classifier is used. In some implementations, the neural network-based non-linear classifier is configured to map individual pixels from the generated tomographic images to a binary prediction for PAH (i.e., the condition exists or does not exist) as well as more generally to PH and other PH subgroups of diseases (e.g., PH due to left heart disease; PH relating to lung disease or hypoxia; chronic thromboembolic pulmonary hypertension; and various rare disorders that lead to PH). In some implementations, the neural network's weights, which govern this mapping, is optimized using gradient descent techniques.

In some implementations, more than one phase space volumetric objects 112a/b are generated and evaluated from a single phase-gradient biophysical data set 108 acquired in a single acquisition session. For example, if a phase-gradient biophysical data set is acquired over about 210 seconds, and a set of phase space volumetric objects 112a/b is generated from about 30 seconds of data, then multiple phase space volumetric objects 112a/b (e.g., one to seven) could be generated and analyzed from non-overlapping portion of the phase-gradient biophysical data set.

In some implementations, a neural network classifier containing a plurality of hidden neurons (e.g., 15 neurons or more) with leaky rectified linear activations is used. Dropout may be used between the hidden layer and the final output neuron, in some implementations, to prevent overfitting. L1 and L2 regularization penalties may also be applied. Binary cross entropy may be used as a loss function, and optimization maybe performed using a gradient-based Adam algorithm.

Figures 6A, 6B:
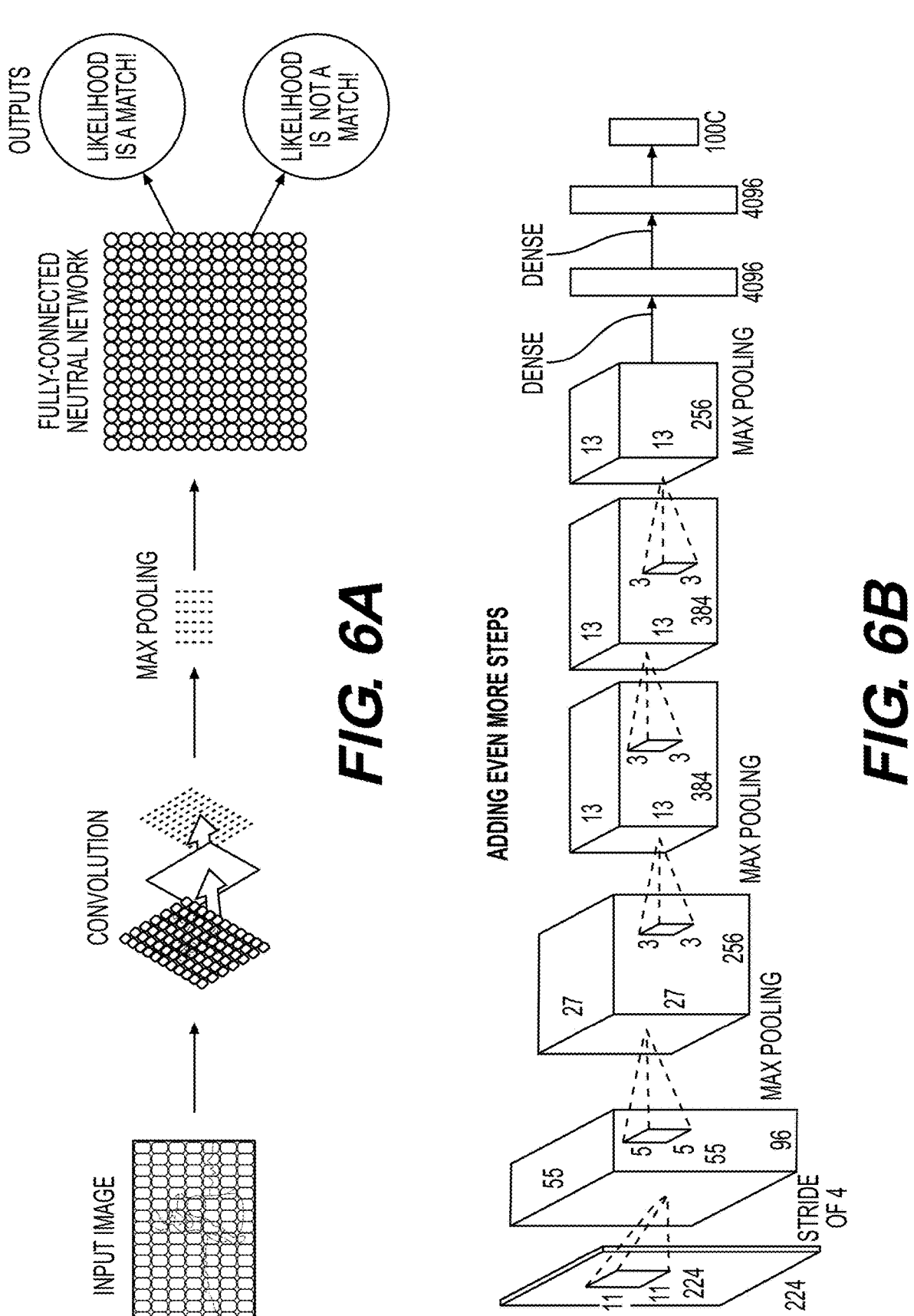
FIGS. 6A and 6B illustrate aspects of a convolution neural network.

In some implementations, the neural network may be a deep leaning convolving neural network (CNN), as shown in FIGS. 6A and 6B. A CNN creates its own feature space, which is suitable for images analysis. A CNN makes use of many branches of math, including Category Theory, Graph Theory and directed graphs.

Biopotential-Based Measurement Equipment and Sensors

Figure 1A:
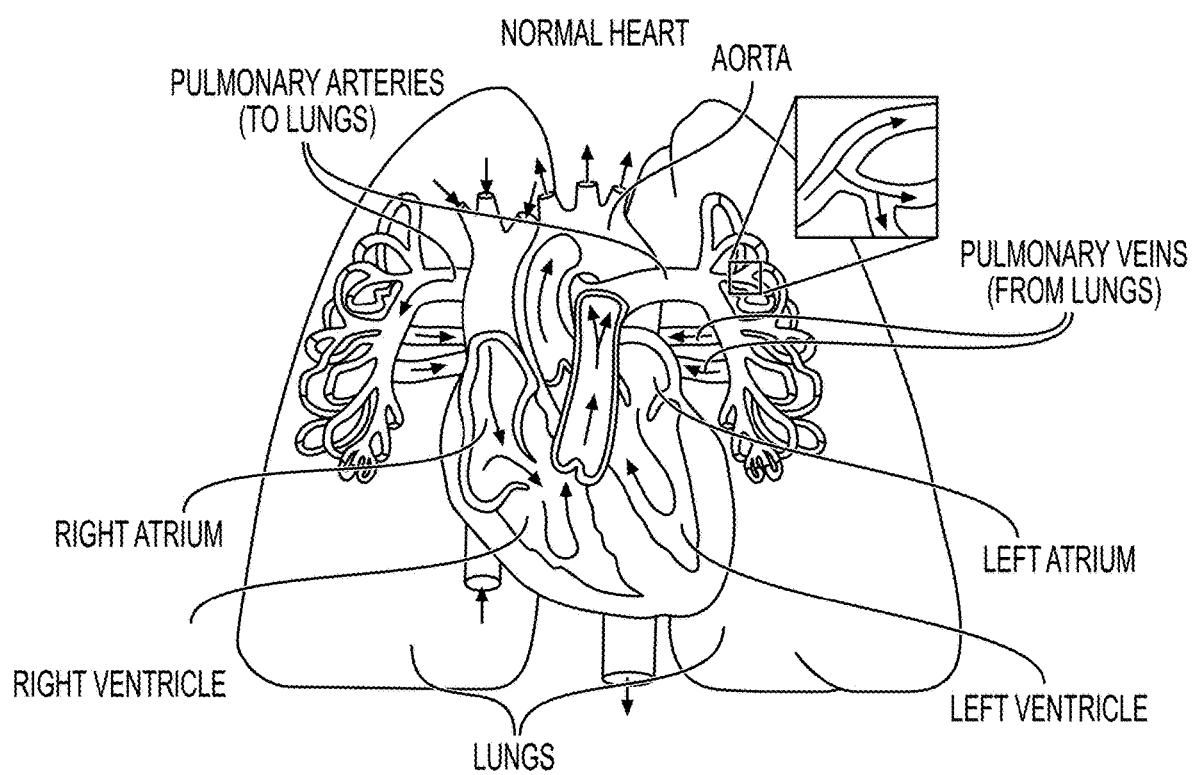
FIGS. 1A and 1B, show a comparison of a first subject having a normal heart with a second subject having pulmonary arterial hypertension.
Figure 1B:
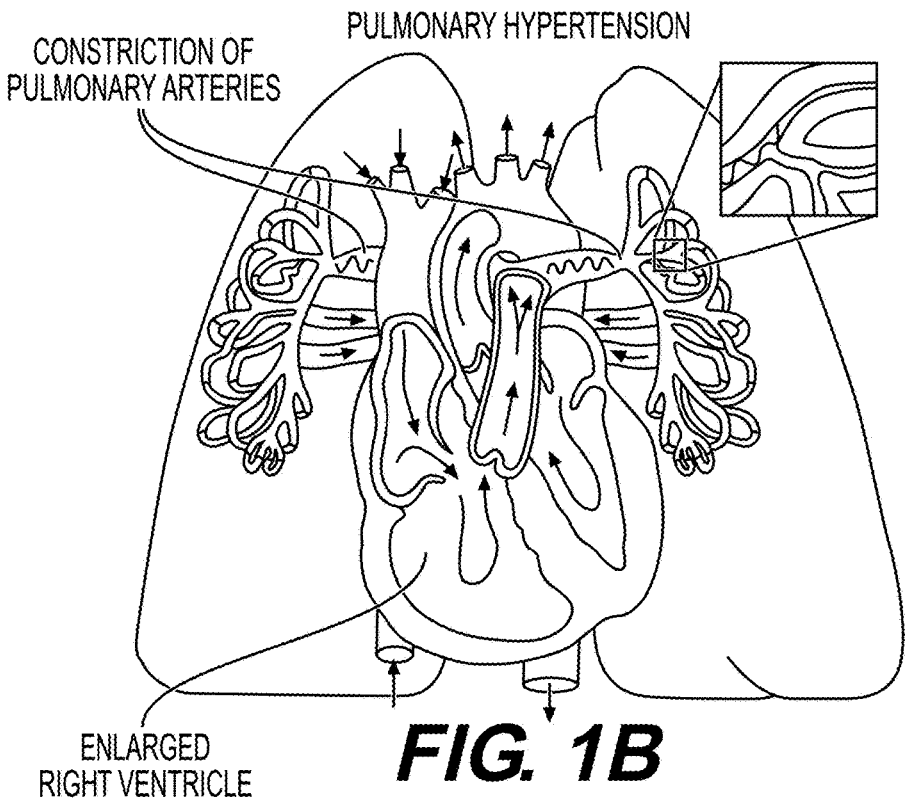

Referring again to the implementation of FIG. 1, system 100 includes biopotential-based measurement equipment 102 which, in some implementations, is wide-band biopotential measuring equipment that, in the cardiography context, captures cardiac-related biopotential or electrophysiological signals of a mammalian subject such as a human as wide-band cardiac phase gradient signals. Such equipment 102 may capture other mammalian biopotential or electrophysiological signals, such as, e.g., neurological biopotential signals.

As described in U.S. Publication No. 2017/0119272 and in U.S. patent application Ser. No. 15/248,838, each of which is incorporated by reference herein in its entirety, the biopotential-based measurement equipment 102, in some implementations, is configured to capture unfiltered mammalian electrophysiological signals such that the spectral component(s) of the signals are not altered. That is, all of the captured signal, if not a significant portion of the captured signal, includes, and does not exclude, components conventionally perceived/treated as and filtered out as noise (e.g., including those in the frequency range of greater than about 1 kHz). Further, the biopotential-based measurement equipment 102 of FIG. 1 can capture, convert, and even analyze the collected wide-band biopotential signals without any filtering (via, e.g., hardware circuitry and/or digital signal processing techniques, etc.) that otherwise can affect the phase linearity of the signal of interest in the wide-band biopotential signals.

In some implementations, the biopotential-based measurement equipment 102 include wide-band equipment configured to capture one or more biosignals of a subject, such as mammalian biopotential signals, in microvolt or sub-microvolt resolutions that are at, or significantly below, the noise floor of conventional electrocardiographic and other biosignal acquisition instruments. In some implementations, the wide-band biopotential measuring equipment is configured to acquire and record wide-band phase gradient signals (e.g., wide-band cardiac phase gradient signals, wide-band cerebral phase gradient signals) that are simultaneously sampled, in some implementations, having a temporal skew or "lag" of less than about 1 μs, and in other implementations, having a temporal skew or lag of not more than about 10 femtoseconds. Notably, the exemplified system minimizes non-linear distortions (e.g., those that can be introduced via certain filters) in the acquired wide-band phase gradient signal so as to not affect the information therein.

Phase Space Transformation and Analysis

As described in U.S. patent application Ser. No. 15/633,330, a phase space analysis system is configured to generate a phase space map to be used to non-invasively measure myocardial ischemia based on features extracted from such phase space map.

Multi-dimensional residue subspace dataset can be generated as a residue (e.g., a subtraction operator) of two wavelet operators. The first wavelet operator may be the wavelets cleaning, for example, using the biorthogonal wavelet 3.3 operator. The second wavelet operator may be a Reverse Biorthogonal Wavelet 3.7 operator.

Figure 7:
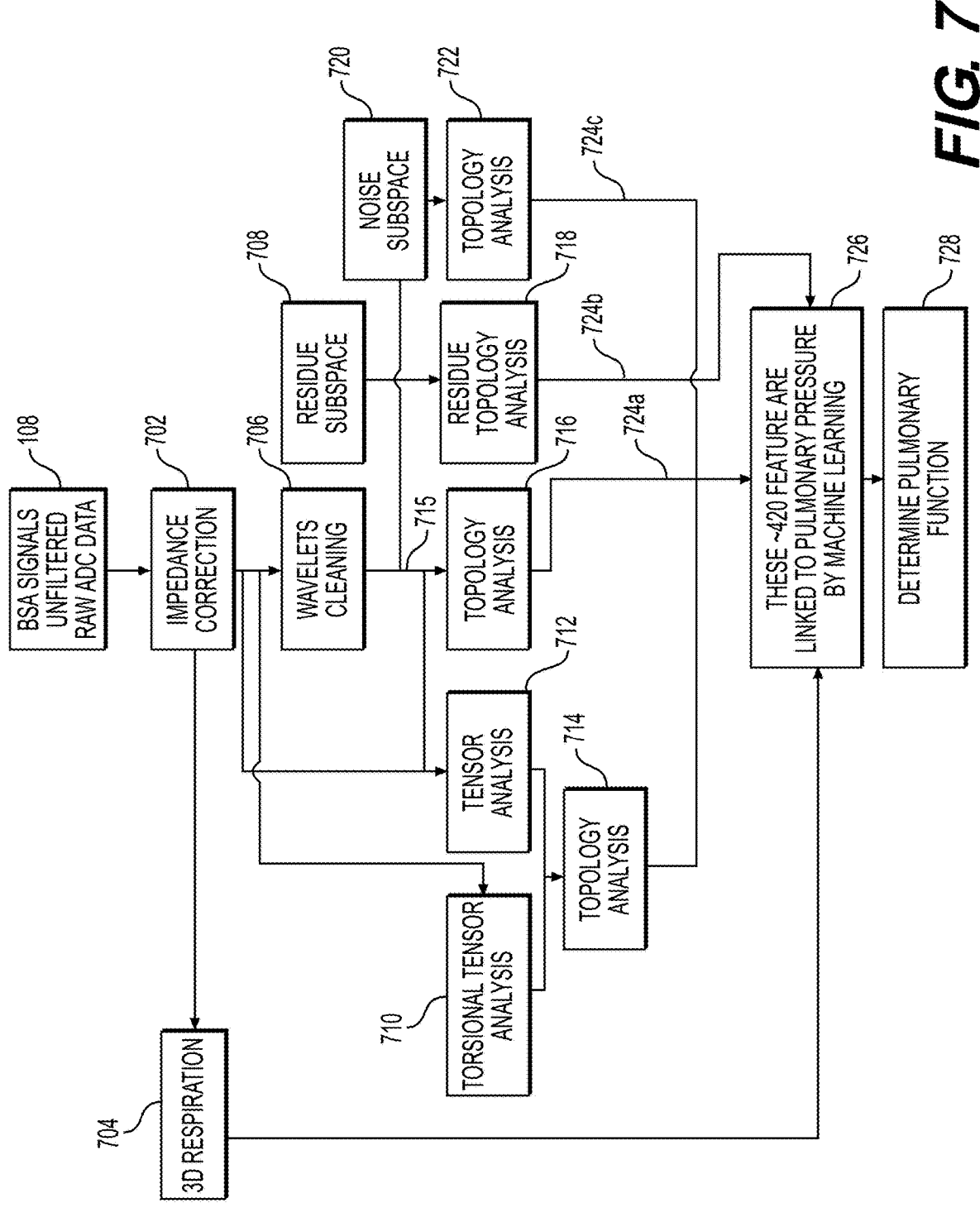
FIG. 7 is a diagram of an exemplary method of processing the phase-gradient biophysical data set in accordance with an illustrative implementation.
Figure 8:
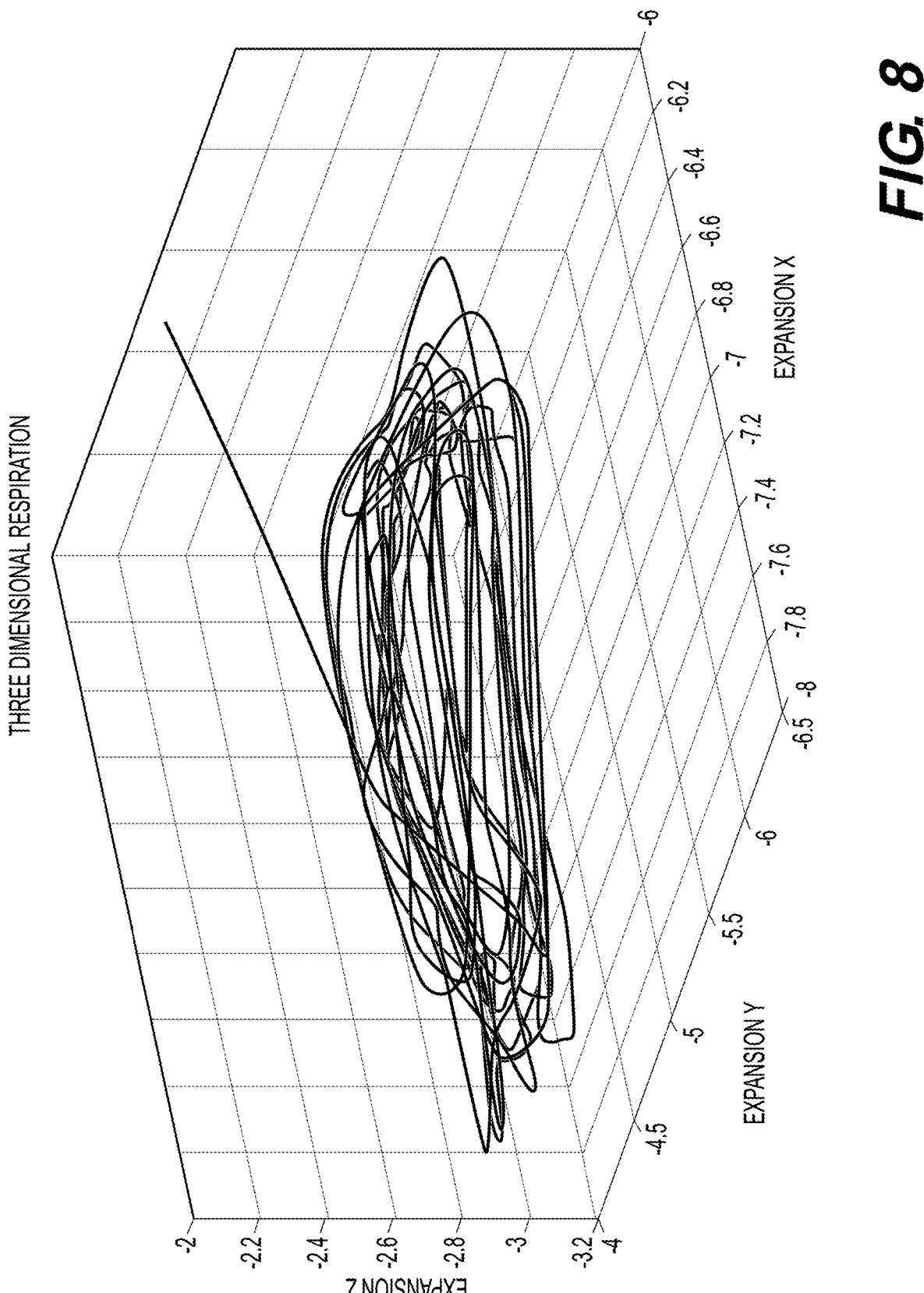
FIG. 8 illustrates a 3D respiration wave.
Figure 9A:
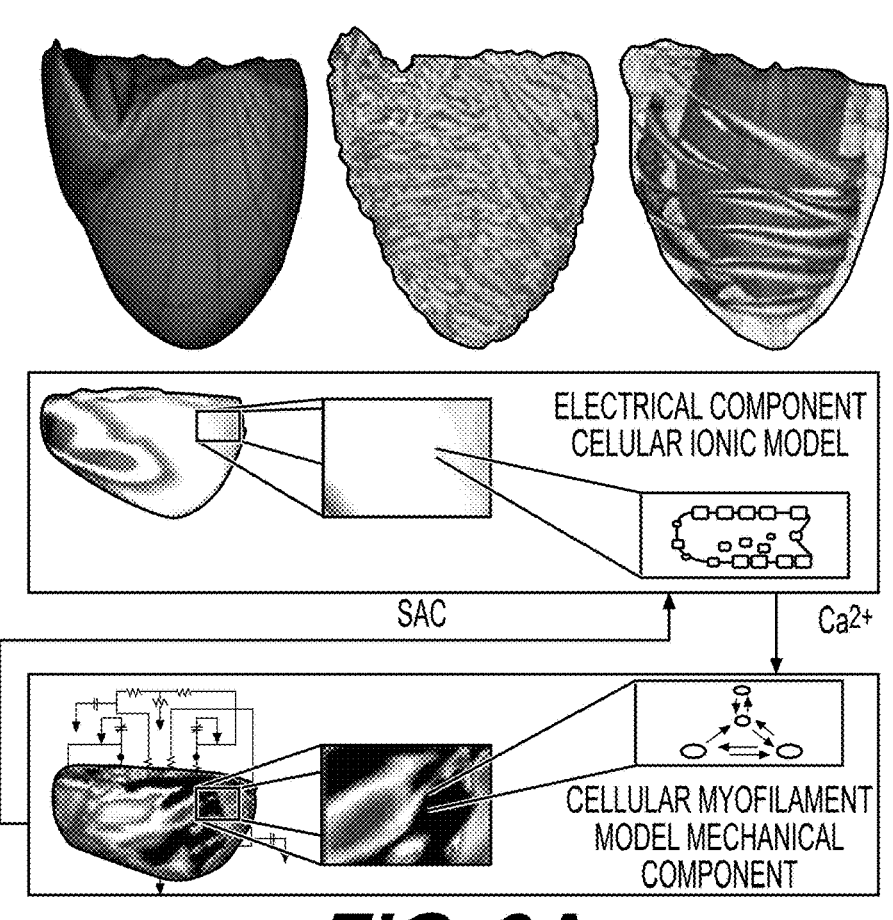
FIGS. 9A and 9B illustrate mechanoelectric transduction and torsional/translations tensors.
Figure 9B:
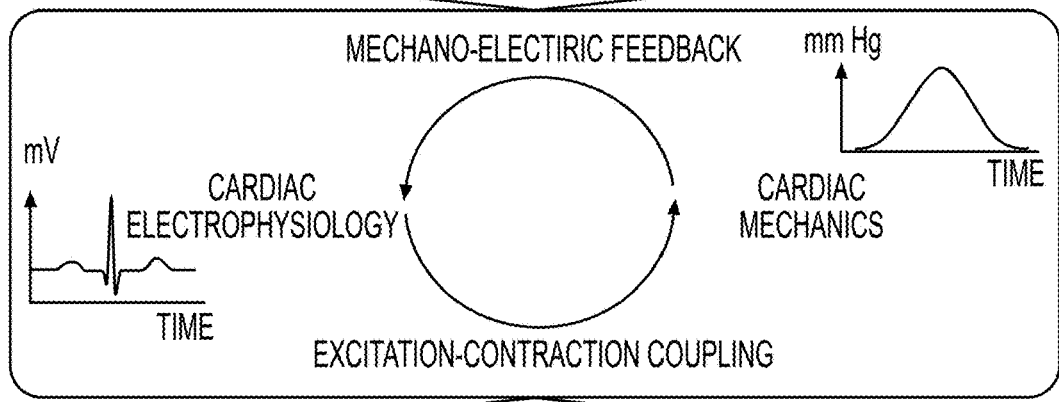
Figure 10:
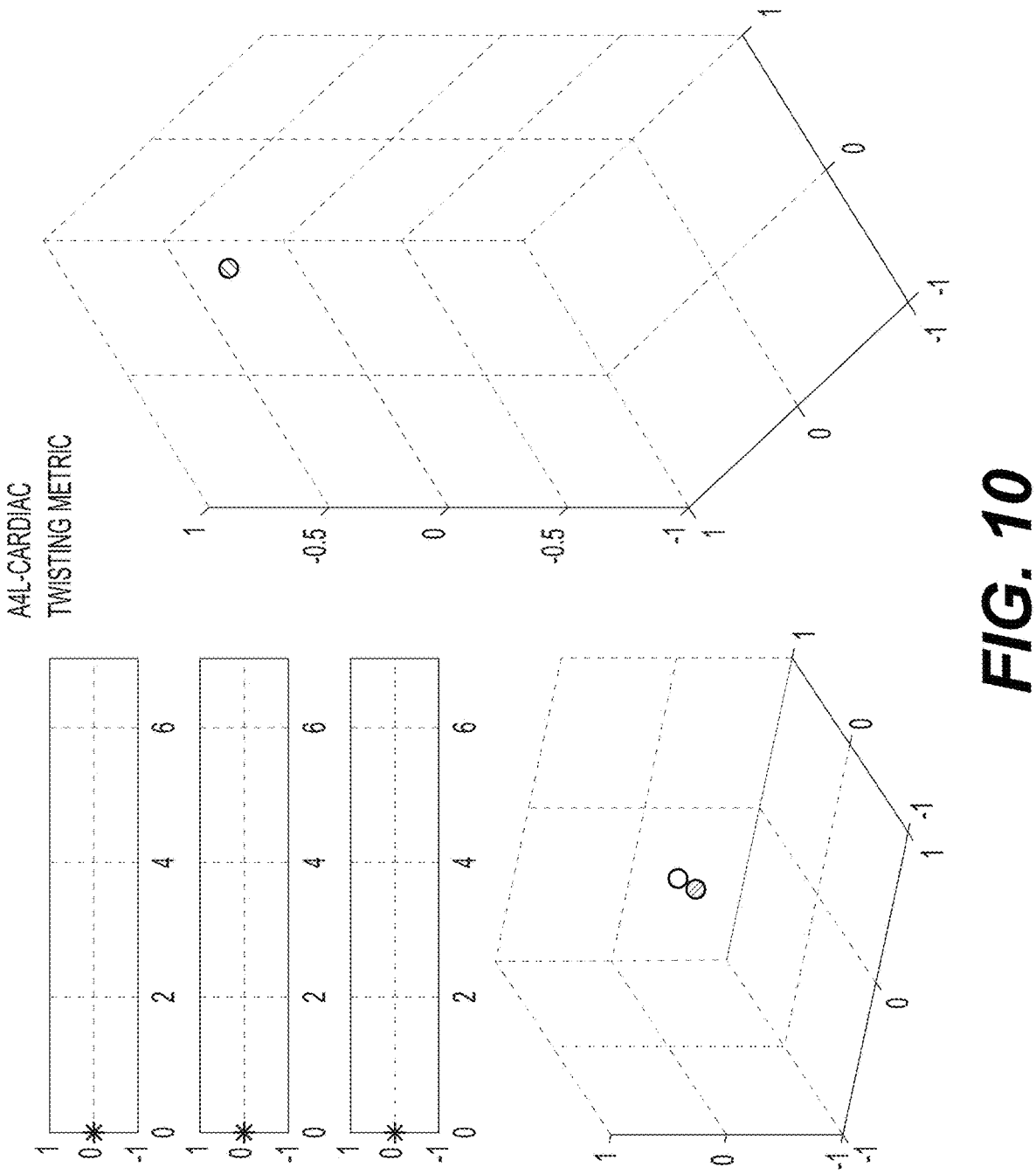
FIG. 10 illustrates an example showing evaluating cardiac twist.

Referring still to FIG. 7, each residue output of the wavelet operator and wavelet operator for each of the gradient signals are combined and transformed, via phase space transformation, to produce the multi-dimensional residue subspace dataset. Feature topology analysis may be performed on the multi-dimensional wavelet residue dataset to extract metrics and variables. The extracted metrics and variables may include morphological, topologic, or functional features of the multi-dimensional wavelet residue dataset including, for example, 3D volume value, a void volume value, a surface area value, a principal curvature direction value, and a Betti number value. In some embodiments, the multi-dimensional wavelet cleansed dataset may be segmented, or partitioned, into sub-regions to which metrics and variables of these sub-regions are extracted. In some embodiments, a void volume value, a surface area value, a principal curvature direction value, and a Betti number value is also determined for each sub-region. In some embodiments, the number of generated sub-regions (also referred to as number of segments) is between 2 and about 20 (e.g., 2, 3, 4, 5, 6, 7, 8, 9, 10, 11, 12, 13, 14, 15, 16, 17, 18, 19, and 20). In some embodiments, the number of subregions is greater than 20. In some embodiments, a similar or same topology extraction analysis may be performed.

FIG. 7 is a diagram of an exemplary method 700 of processing the phase-gradient biophysical data set 108 in accordance with an illustrative implementation. The method 700 includes collecting and phase-gradient biophysical data set 108 to generate, via phase space analysis techniques, a phase space dataset (shown as input data 715, "residue subspace" dataset 708 and "noise subspace" dataset 720). Impedance correction 702 is applied to the input signals to correct imbalances in the acquisition leads from which the phase-gradient biophysical data is collected.

As shown in FIGS. 8, 9A, 9B and 10, attributes of 3D respiration 704 may be determined from the impedance-corrected phase-gradient biophysical data set 108 as the metric space characterizes etiologic factors are provided by mechanoelectric transduction feedback. This information is provided as an output 726, described below. In addition, the impedance-corrected phase-gradient biophysical data set 108 a torsional tensor analysis (710) and a translational tensor analysis (712) is applied. The torsional and translational tensor features characterize raw cardiac dynamics.

The characteristics of the phase space data set (608, 720), the input data set (615) and the torsional tensor analysis 710 and tensor analysis 712 may be extracted, in a feature extraction operation (e.g., analysis steps 714, 716, 718, 722) to determine geometric and dynamic properties of the data set. These subspaces may include, but are not limited to complex subharmonic frequency (CSF) trajectory, quasi-periodic and chaotic subspaces, low/high energy subspaces, and fractional derivatives of the low/high energy subspaces. These subspaces are exemplars of the family of subspaces that characterize the dynamics of the system, whether pathological or normal. In some implementations, the extracted metrics are generated from the phase space volumetric object 112a/b and generated from one or more of the phase space data sets (708, 720), the input data set (615), the torsional tensor analysis (710) and/or the tensor analysis (712).

As shown in FIG. 7, one or more of the phase space data sets (608, 720), the input data set (715), the torsional tensor analysis (710) and/or the tensor analysis (712), in some implementations, are evaluated via fractional derivative operations to generate point cloud data set to which faces are generated via triangulation. In some implementations, one or more color map data sets are generated for the determined vertex data set. Metrics (e.g., extracted metrics 724*a*, 724*b*, 724*c*) are assessed including a volume metric (e.g., alpha hull volume), a number of distinct bodies (e.g., distinct volumes), and/or a maximal color variation (e.g., color gradient) of the generated phase space volumetric object 112*a/b*.

Analysis using phase space analysis techniques as described herein can facilitate understanding of different bioelectric structures within mammalian tissue, including but not limited to tissue in or associated with organs such as the brain or the heart and their related systems. For example, various types of cardiac tissue, particularly but not necessarily when such tissue is/are damaged or unhealthy, may exhibit different conduction characteristics, such as can be exhibited by differences in tissue impedance. Indeed, these techniques can be used to understand spectral and non-spectral conduction delays and bends in the trajectory of the phase space orbit as it propagates through the heart. These small changes in trajectory can further be normalized and quantified on a beat-to-beat basis and corrected for abnormal or poor lead placement. The normalized phase space integrals can also be visualized on, or mapped to, a geometric mesh (e.g., a model of the heart) using a genetic algorithm. In some implementations, these phase space integrals are mapped to myocardial segments in the heart. In some implementations, these mapped myocardial segments can correspond to the 17-segments of the left ventricular model of the heart. Other number of myocardial segments may be used.

Referring still to FIG. 7, three distinct phase space analyses are performed to generate sets of metrics and variables (shown as steps 724*a*, 724*b*, 724*c*). The metrics and variable are then used in the non-linear functions (e.g., as shown in step 724) to generate regional estimation values representative of pulmonary arterial hypertension.

The output of the phase space analysis (726) may be features that are linked to PH, and more specifically in one example PAH, which are evaluated using machine learning analysis to assess parameters associated with a presence and/or degree of a disease or physiological characteristic (such as, e.g., in the cardiovascular context, regional arterial flow characteristics). For example, 420 features may be evaluated. The features may be optimized for right heart and respiration function. In some implementations, the machine learning analysis may use a library of quantified PAH data (e.g., data acquired from a study of coronary arterial disease) in the assessment of the obtained wide-band cardiac gradient signal data. The result of the machine learning analysis is a determination of pulmonary function (728). In some implementations, the output may be a unit-less prediction of PAH. The operational flow of FIG. 7 may operate continuously whereby a threshold is applied to the continuous output to make a determination of PAH.

The output 728 (e.g., an output of a processor performing the analysis) may then be transmitted to a graphical user interface, such as, e.g., a touchscreen or other monitor, for visualization. The graphical user interface, in some implementations, is included in a display unit configured to display values of any number of parameters discussed herein and elsewhere. In some implementations, the graphical user interface displays these data in formats such as, e.g., a three-dimensional phase space plot representation of the biopotential signal data and virtual biopotential signal data. In other implementations, the data output of the processor is or may also be simultaneously or sequentially transmitted to one or more non-graphical user interfaces (e.g., printout, command-line or text-only user interface), directly to a database or memory device, processor, firmware, hardware and/or software for, e.g., later retrieval and/or additional analysis, other machines that may include non-graphical user interfaces for the display of such data, or combinations thereof. Any device, machine, or medium capable of receiving data and being interpreted by a human or machine or used for further processing is contemplated and within the scope of the present disclosure.

A visualization engine may receive the determined arterial flow characteristics and renders the characteristics onto a three-dimensional visualization output. In some implementations, the visualization engine provides, in a graphical user interface (GUI), a system-level view of the arterial flow characteristics and their interactions. In some implementations, the GUI presents the cascading effects of upstream modifications to the arterial flow upon the downstream circulation. Further description of an example visualization engine is provided in U.S. application Ser. No. 15/712,104, title "Method and System for Visualization of Heart Tissue at Risk", which is incorporated by reference herein in its entirety.

Further examples of phase space processing that may be used with the exemplified method and system are described in U.S. Publication No. 2016/0378936, title "Methods and Systems Using Mathematical Analysis and Machine Learning to Diagnose Disease"; U.S. Publication No. 2015/0216426, title "Method and System for Characterizing Cardiovascular Systems From Single Channel Data"; U.S. Pat. No. 9,597,021, title "Noninvasive Method for Estimating Glucose, Glycosylated Hemoglobin and Other Blood Constituents"; U.S. Publication No. 2015/0133803, title "Noninvasive Electrocardiographic Method for Estimating Mammalian Cardiac Chamber Size and Mechanical Function"; U.S. Pat. No. 9,737,229, title "Noninvasive Electrocardiographic Method for Estimating Mammalian Cardiac Chamber Size and Mechanical Function"; U.S. Pat. No. 9,408,543, title "Non-invasive Method and System for Characterizing Cardiovascular Systems and All-Cause Mortality and Sudden Cardiac Death Risk"; U.S. Pat. No. 9,655,536, title "Non-invasive Method and System for Characterizing Cardiovascular Systems"; U.S. Pat. No. 9,289,150, title "Non-invasive Method and System for Characterizing Cardiovascular Systems"; U.S. Pat. No. 8,923,958, title "System and Method for Evaluating an Electrophysiological Signal"; U.S. Publication No. 2017/0119272, title "Method and Apparatus for Wide-Band Phase Gradient Signal Acquisition"; U.S. application Ser. No. 15/633,330, title "Non-invasive Method and System for Measuring Myocardial Ischemia, Stenosis Identification, Localization and Fractional Flow Reserve Estimation"; and U.S. application Ser. No. 15/712,104, title "Method and System for Visualization of Heart Tissue at Risk"; U.S. application Ser. No. 16/165,641, title "Methods and Systems of De-Noising Magnetic-Field Based Sensor Data of Electrophysiological Signals"; U.S. application Ser. No. 16/232,586, title "Method and System to Assess Disease Using Phase Space Tomography and Machine Learning"; U.S. application Ser. No. 15/653,433, title "Discovering Novel Features to Use in Machine Learning Techniques, such as Machine Learning Techniques for Diagnosing Medical Conditions"; and U.S.

application Ser. No. 15/653,431, title "Discovering Genomes to Use in Machine Learning Techniques"; each of which are incorporated by reference herein in its entirety.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of implementations described in the specification.

While the methods and systems have been described in connection with certain implementations and specific examples, it is not intended that the scope be limited to the particular implementations set forth, as the implementations herein are intended in all respects to be illustrative rather than restrictive.

Examples of other biophysical signals that may be analyzed in whole, or in part, using the exemplary methods and systems include, but are not limited to, an electrocardiogram (ECG) data set, an electroencephalogram (EEG) data set, a gamma synchrony signal data set; a respiratory function signal data set; a pulse oximetry signal data set; a perfusion data signal data set; a quasi-periodic biological signal data set; a fetal ECG data set; a blood pressure signal; a cardiac magnetic field data set, and a heart rate signal data set.

The exemplary analysis can be used to identify various pathologies and condition including, but are not limited to heart disease, cardiac arrhythmia, diabetic autonomic neuropathy, Parkinson's disease, forms of epilepsy, brain injury, altered state of cognition, stability of a heart at different heart rates, effectiveness of medication, ischemic, silent ischemia, atrial fibrillation, ventricular fibrillation, ventricular tachycardia, blood vessel block, attention deficit disorder, etc.

What is claimed is:

1. A method for non-invasively assessing presence or non-presence of pulmonary hypertension, the method comprising:

obtaining, by one or more processors, acquired data from a measurement of one more biophysical signals of a subject, wherein the acquired data is derived from measurements acquired via noninvasive equipment configured to measure properties of a heart;

generating, by the one or more processors, a phase space data set from the acquired data;

performing, by the one or more processors, a residue topology analysis on the phase space data set to generate one or more metrics;

generating, by the one or more processors using a machine learning algorithm, one or more predictors linking aspects of the one or more metrics across a population of patients representing both positive and negative cases to detect the presence of pulmonary hypertension; and outputting, via one or more an output data set, the one or more predictors, wherein the output is subsequently used for an assessment of presence and/or non-presence of pulmonary hypertension.

2. The method of claim 1, wherein the phase space data set comprises a residue subspace data set and a noise subspace data set.

3. The method of claim 1, further comprising applying impedance correction to the acquired data.

4. The method of claim 1, further comprising determining one or more metrics of the phase space data set, wherein the one or more metrics include one or more of: complex frequency trajectory, quasi-periodic and chaotic subspaces, low/high energy subspaces, and fractional derivatives of the low/high energy subspaces.

5. The method of claim 4, further comprising performing a torsional tensor analysis on the phase space data set and determining the one or more metrics from the torsional tensor analysis.

6. The method of claim 4, further comprising performing a tensor analysis on the phase space data set and determining the one or more metrics from the tensor analysis.

7. The method of claim 1, further comprising:

evaluating the phase space data set using fractional derivative operations to generate a point cloud data set;

generating a phase space volumetric object using the point cloud data set.

8. The method of claim 7, further comprising:

determining a set of tomographic images from the phase space volumetric object; and generating the one or more predictors based on the set of tomographic images using a trained neural network classifier.

9. The method of claim 7, further comprising determining one or more metrics from the phase space volumetric object and the phase space data set.

10. The method of claim 9, wherein the one or more metrics determined from the phase space volumetric object include a volume metric, a distinct bodies metric, and a maximal color variation metric.

11. The method of claim 1, wherein generating the one or more predictors comprises:

using one or more non-linear functions on the one or more metrics to generate the one or more predictors.

12. The method of claim 1, wherein the acquired data comprises wide-band cardiac gradient signal data.

13. The method of claim 1, wherein the acquired data comprises a phase-gradient biophysical data set.

14. The method of claim 13, further comprising:

determining a plurality of non-overlapping portions of the phase-gradient biophysical data set; and generating a phase space volumetric object from each non-overlapping portion of the plurality of non-overlapping portions.

15. The method of claim 13, further comprising generating the one or more predictors based on one or more of the generated phase space volumetric objects.

16. The method of claim 1, further comprising:

determining attributes of a 3D respiration wave from the acquired data; and generating the one or more predictors based on the phase space data set and the determined attributes of the 3D respiration wave.

17. The method of claim 1, wherein the acquired data comprises differential channel signals.

18. The method of claim 1, wherein the assessment of presence and/or non-presence of pulmonary hypertension is selected from the group consisting of: an assessment of pulmonary arterial hypertension; an assessment of pulmonary hypertension due to left heart disease; an assessment of pulmonary hypertension relating to lung disease or hypoxia;

an assessment of pulmonary hypertension includes chronic thromboembolic pulmonary hypertension; and an assessment of a rare disorder that leads to pulmonary hypertension.

19. A system comprising:

a processor; and a memory having instructions stored thereon, wherein the instructions when executed by the processor cause the system to:

obtain acquired data from a measurement of one more biophysical signals of a subject, wherein the acquired data is derived from measurements acquired via non-invasive equipment configured to measure properties of a heart;

generate a phase space data set from the acquired data;

perform a residue topology analysis on the phase space data set to generate one or more metrics;

generate, using a machine learning algorithm, one or more predictors linking aspects of the one or more metrics across a population of patients representing both positive and negative cases to detect the presence of pulmonary hypertension; and output, via one or more of an output data set, the one or more predictors, wherein the output is subsequently used for an assessment of presence and/or non-presence of pulmonary hypertension.

20. A non-transitory computer readable medium having instructions stored thereon, wherein execution of the instructions by a processor, cause the processor to:

obtain acquired data from a measurement of one more biophysical signals of a subject, wherein the acquired data is derived from measurements acquired via non-invasive equipment configured to measure properties of a heart;

generate a phase space data set from the acquired data;

perform a residue topology analysis on the phase space data set to generate one or more metrics;

generate, using a machine learning algorithm, one or more predictors linking aspects of the one or more metrics across a population of patients representing both positive and negative cases to detect the presence of pulmonary hypertension; and output, via one or more of an output data set, the one or more predictors, wherein the output is subsequently used for an assessment of presence and/or non-presence of pulmonary hypertension.

* * * * *